(12) United States Patent
Blanski et al.

(10) Patent No.: US 10,919,860 B2
(45) Date of Patent: *Feb. 16, 2021

(54) BACKFUNCTIONALIZED IMIDAZOLINIUM SALTS AND NHC CARBENE-METAL COMPLEXES

(71) Applicant: Government of the United States as Represented by the Secretary of the Air Force, Wright-Patterson AFB, OH (US)

(72) Inventors: Rusty L. Blanski, Palmdale, CA (US); Robert H. Grubbs, South Pasadena, CA (US)

(73) Assignee: United States of America as represented by the Secretary of the Air Force, Wright-Patterson AFB, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/548,419

(22) Filed: Aug. 22, 2019

(65) Prior Publication Data

US 2020/0002286 A1 Jan. 2, 2020

Related U.S. Application Data

(60) Continuation of application No. 16/103,267, filed on Aug. 14, 2018, which is a division of application No. 15/725,848, filed on Oct. 5, 2017, now Pat. No. 10,214,494, which is a division of application No. 14/880,147, filed on Oct. 9, 2015, now Pat. No. 9,828,347.

(60) Provisional application No. 62/062,069, filed on Oct. 9, 2014.

(51) Int. Cl.
C07D 233/28 (2006.01)
C07F 15/00 (2006.01)

(52) U.S. Cl.
CPC ........ *C07D 233/28* (2013.01); *C07F 15/0033* (2013.01); *C07F 15/0046* (2013.01)

(58) Field of Classification Search
CPC .................................................. C07D 233/28
See application file for complete search history.

(56) References Cited

U.S. PATENT DOCUMENTS

| | | |
|---|---|---|
| 5,789,027 A | 8/1998 | Watkins et al. |
| 7,622,590 B1 | 11/2009 | Nolan et al. |
| 7,902,389 B2 | 3/2011 | Nolan et al. |
| 8,703,965 B2 | 4/2014 | Kuhn et al. |
| 8,877,936 B2 | 11/2014 | Grubbs et al. |
| 10,538,494 B2 * | 1/2020 | Blanski ............... C07F 15/0046 |
| 2011/0087032 A1 | 4/2011 | Kuhn et al. |
| 2013/0225807 A1 | 8/2013 | Skowerski et al. |
| 2014/0182680 A1 | 7/2014 | Kawata et al. |
| 2015/0004322 A1 | 1/2015 | Blanski |

FOREIGN PATENT DOCUMENTS

| | | |
|---|---|---|
| DE | 102004039277 | 2/2006 |
| DE | 102008043344 | 5/2010 |
| WO | 2007017047 | 2/2007 |

OTHER PUBLICATIONS

N. Duguet et al., "Chiral relay in NHC-mediated asymmetric beta-lactam synthesis II; asymmetry from NHCs derived from acyclic 1,2-diamines," Tetrahedron:Asymmetry, vol. 21 (2010) 601-616.

Y. Matsumoto et al., "C2 symmetric chiral NHC ligand for asymmetric quaternary carbon constructin gcopper-catalyzed conjugate addition of Grignard reagents to 3-substituted cyclohexenones," JOC, vol. 73 (2008) 4578-4581.

I. Laios et al., "Effects of (R,S)/(S,R)-4,5-bis(2-chloro-4-hydroxyphenyl)-2-imidazolines and (R,S)/(S,R)-2,3-bis(2-chloro-4-hydroxyphenyl)piperazines on estrogen receptor alpha level and transcriptional activity in MCF-7 cells," Biochemical Pharmacology, vol. 74 (2007) 1029-1038.

O. Sereda et al., "Enantiopure imidazolinium-dithiocarboxylates as highly selective novel organocatalysts," ChemComm. (2009) 1040-1042.

T. Arao et al., "Function of an N-heterocyclic carbene ligand based on concept of chiral mimetic," Chem.Pharm. Bull, vol. 54 (2006) 1576-1581.

L. Delaude et al., "New in situ generated ruthenium catalysts bearing N-heterocyclic carbene ligands for the ring-opening metathesis polymerization of cylooctene," Adv. Syn. Cal., vol. 344 (2002) 749-756.

J. O. Krause et al., "Synthesis and reactivity of homogeneous and heterogeneous ruthenium-based metathesis catalysts containing electron-withdrawing ligands," Chem. Eur. J., vol. 10 (2004) 777-784.

(Continued)

*Primary Examiner* — Paul V Ward
(74) *Attorney, Agent, or Firm* — AFMCLO/JAZ; Chastity D. S. Whitaker

(57) ABSTRACT

Backfunctionalized imidazolinium salts and methods of synthesizing the same and NHC carbene-metal complexes therefrom. For backfunctionalized imidazolinium salts of the formula:

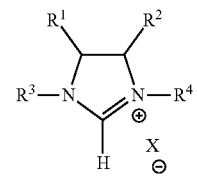

Wherein $R^1$ is selected from the group consisting of an ester group, an amide group, and an aromatic group; $R^2$ is selected from the group consisting of hydrogen, an ester group, an amide group, and an aromatic group; $R^3$ and $R^4$ are each an aliphatic group; and
X is an anion; the method comprises cyclization of a halogenated acrylate with Hünig's base in a solvent.

6 Claims, 18 Drawing Sheets

(56) References Cited

OTHER PUBLICATIONS

R. C. Da Costa et al., "Synthesis and reactivity of analogues of Grubbs' second generation metathesis catalyst with fluorous phosphines: a new phase-transfer strategy for catalyst activation," Adv. Synth. Catal., vol. 349 (2007) 243-254.
Q. Yao et al., "Poly(fluoroalkyl acrylate)-bound ruthenium carbene complex: a fluorous and recyclable catalyst for ring-closing olefin metathesis," JAGS, vol. 126 (2004) 74-75.
A. Forstner et al., "Comparative investigation of ruthenium-based metathesis catalysts bearing N-heterocyclic carbene (NHC) ligands," Chem. Euro. J., vol. 7 (2001) 3236-3253.
M. Rezanka et al., "Synthesis of mono(perfluoroalkyl) cyclodextrins via cross metathesis," Eur. J. Org. Chem., vol. 32 (2010) 6256-6262.
B. Eignerova et al., "Synthesis of perfluoroalkylated carboranes by cross-metathesis of allylcarboranes and perfluoroalkylpropenes," Synlett, vol. 6 (2010) 885-888.
K. M. Kuhn et al., "A facile preparation of imidazolinium chlorides," Org. Lett., vol. 10 (2008) 2075-2077.
M. Iglesias et al., "Novel expanded ring N-heterocyclic carbenes: free carbenes, silver complexes, and structures," Organomel., vol. 27 (2008) 3279-3289.
D. P. Allen et al., "Well-defined silica-supported olefin metathesis catalysts," Org. Lett., vol. 11 (2009) 1261-1264.
S. C. Schurer et al., "Synthesis and application of a permanently immobilized olefin-metathesis catalyst," Angew. Chem. Int. Ed., vol. 39 (2000) 3898-3901.
J. M. Blackburn et al., "Deposition of conformal copper and nickel films from supercritical carbon dioxide," Science, vol. 294 (2001) 141-145.
A. Cabanas et al., "Deposition of Cu films from supercritical fluids using CuII) beta-diketonate precursors," Microelecl. Eng., vol. 64 (2002) 53-61.
C. F. Karanikas et al., "Kinetics of the ruthenium thin film deposition from supercritical carbon dioxide by the hydrogen reduction of Ru(tmhd)2cod," Microelect Eng., vol. 87 (2010) 566-572.
O. Aschenbrenner et al., "Solubility of beta-diketonates, cyclopentadienyls, and cyclooctadiene complexes with various metals in supercritical carbon dioxide," J. Supercrit. Fluids, vol. 41 (2007) 179-186.
J. W. Sprengers et al., "Palladium-(N-heterocylic carbene hydrogenation catalysts," Angew. Chem. Int., vol. 44 (2005) 2026-2029.
R. H. Crabtree et al., "Cationic iridium diolefin complexes as alkene hydrogenation catalysts and the isolation of some related hydride complexes," J. Organomet. Chem., vol. 141 (1977) 205-215.
M. T. Powell et al., "Chiral imidazolylidine ligands for asymmetric hydrogenation of aryl alkenes," JAGS, vol. 123 (2001) 8878-8879.
H. M. Lee et al., "A cationic iridium complex bearing an imidazol-2-ylidene ligand as alkene hydrogenation catalyst," Organomel., vol. 20 (2001) 1255-1258.
S. Diez-Gonzalez et al., "N-heterocyclic carbenes in late transition metal catalysis," Chem. Rev., vol. 109 (2009) 3612-3676.
J. A. Darr et al., "New directions in inorganic and metal-organic coordination chemistry in supercritical fluids," Chem. Rev., vol. 99 (1999) 495-542.
G. C. Vougioukalakis et al., "Ruthenium-based heterocyclic carbene-coordinated olefin metathesis catalysts," Chem. Rev., vol. 110 (2010) 1746-1787.
D. M. Khramov et al., "N-heterocylic carbenes: deducing sigma- and pi-contributions in Rh-catalyzed hydroboration and Pd-catalyzed coupling reactions," Tetrahedron, vol. 64 (2008) 6853-6862.
L. Xu et al., "Fluoroalkylated N-heterocyclic carbene complexes of palladium," J. Organomet. Chem., vol. 598 (2000) 109-416.
M. G. Hobbs et al., "Anionic N-heterocyclic carbenes with N, N'-bis(fluoroaryl) and N,N'-bis(perfluoroaryl) substituents," Chem. Eur. J., vol. 16 (2010) 14520-14533.
J. W. Ogle et al., "Synthesis of electronically diverse tetraarylimidazolylidene carbenes via catalytic aldimine coupling," Org. Lett., vol. 10 (2008) 3677-3680.
T. Ritter et al., "Rate acceleration in olefin metathesis through a fluorine-ruthenium interaction," JAGS, vol. 128 2006) 11768-11769.
M. Skalicky et al., "Synthesis of bis(polyfluoroalkylated)imidazolium salts as key intermediates for fluorous ligands," J. Fluorine Chem., vol. 130 (2009) 966-973.
B. Eignerova et al., "Synthesis and biochemical characterization of a series of 17a-perfluoroalkylated estradiols as selective ligands for estrogen receptor alpha," J. Med. Chem., vol. 53 (2010) 6947-6953.
S. McGrandle et al., "Group 9 complexes of an N-heterocycle carbene bearing a pentafluorobenzyl substituent: attempted dehydrofluorinative coupling of cyclopentadienyl and N-heterocycle carbene ligands," J. Fluorine Chem., vol. 126 (2005) 449-453.
S. Burling et al., "Neutral and cationic fluorinated N-heterocyclic carbene complexes of rhodium and iridium," Organomel., vol. 25 (2006) 3761-3767.
I. T. Horvath et al., "Facile catalyst separation without water: fluorous biphase hydroformylation of olefins," Science, vol. 266 (1994) 72-75.
I. T. Horvath, "Fluorous biphase chemistry," Acc. Chem. Res., vol. 31 (1998) 641-650.
A-F. Mingotaud et al., "Catalytic surfactants for ring-opening metathesis polymerization and ring-closing metathesis in non-degassed micellar solutions," J. Molec. Cal. A: Chemical., vol. 263 (2007) 39-47.
I. C. Stewart et al., "Highly efficient ruthenium catalysts for the formation of tetrasubstituted olefins via ring-closing metathesis," Org. Lett., vol. 9 (2007) 1589-1592.
M-S. Weiser et al., "Colbalt(II) octanoate and cobalt(II) perfluorooctanoate catalyzed atom transfer radical polymerization of styrene in toluene and fluorous media—A versatile route to catalyst recycling and oligomer formation," J. Polym. Chem., Part A, vol. 43 (2005) 3804-3813.
T. Weskamp et al., "A novel class of ruthenium catalysts for olefin metathesis," Angew. Chem., Int. Ed., vol. 37 (1998) 2490-2493.
R. A. Kelly et al., "Determination of N-heterocyclic carbene (NHC) steric and electronic parameters using the [(NHC)Ir(CO)2Cl] system," Organomel., vol. 27 (2008) 202-210.
M. Matsugi et al., "Synthesis, reaction, and recycle of light fluorous Grubbs-Hoveyda catalysts for alkene metathesis," J. Org. Chem., vol. 70 (2005) 1636-1642.
A. K. Chatterjee et al., "Synthesis of functionalized olefins by cross and ring-closing metatheses," JAGS, vol. 122 (2000) 3783-3784.
S. Imhof et al., "Ruthenium catalysed cross metathesis with fluorinated olefins," Chem. Comm., vol. 17 (2001) 1692-1693.
B. Eignerova et al., "Synthesis of fluorinated brassinosteroids based on alkene cross-metathesis and preliminary biological assessment," J. Med. Chem., vol. 52 (2009) 5753-5757.
Patent Translate, English translation of German Patent No. 102008043344, originally published May 6, 2010, translation generated Oct. 9, 2015, 34 pages total.
Patent Translate, English translation of International Application Publication No. 2007/017047, originally published Feb. 15, 2007, translation generated Oct. 9, 2015, 51 pages total.
Patent Translate, English translation of German Patent No. 102004039277, originally published Feb. 23, 2006, translation generated Oct. 9, 2015, 100 pages total.
U.S. Patent and Trademark Office, Non-Final Office Action in U.S. Appl. No. 16/548,444, dated Oct. 19, 2020, 9 pages total.
U.S. Patent and Trademark Office, Non-Final Office Action in U.S. Appl. No. 16/548,472, dated Oct. 19, 2020, 7 pages total.
U.S. Patent and Trademark Office, Non-Final Office Action in U.S. Appl. No. 16/548,501, dated Oct. 19, 2020, 5 pages total.

* cited by examiner

BACKFUNCTIONALIZED IMIDAZOLINIUM SALTS AND NHC CARBENE-METAL COMPLEXES

Pursuant to 37 C.F.R. § 1.78(a)(4), this application is a continuation of U.S. application Ser. No. 16/103,267, filed Aug. 14, 2018, which was a divisional of U.S. application Ser. No. 14/880,147, filed Oct. 9, 2015, which claimed the benefit of and priority to Provisional Application Ser. No. 62/062,069, filed 9 Oct. 2014. The disclosure of each of these applications is expressly incorporated herein by reference, each in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to inorganic carbene complexes and, more particularly, to backfluorinated N-heterocyclic carbene metal complexes.

BACKGROUND OF THE INVENTION

Chemical vapor deposition (hereafter, "CVD") is a conventionally used process for producing high-purity, high-performance materials, such as thin films on semiconductors or growing crystalline structures. Deposition of the films includes exposing a substrate to volatile chemicals, i.e., precursors, which react and/or decompose at a surface of the substrate.

The use of CVD for metal deposition, e.g., organometallic CVD or MOCVD, includes a metal atom (for example, but not limited to, Mo, Ta, Ti, W, Ru, Cu, Pt, and Pd) bonded to organic ligands. However, the CVD process has limitations in that internal structures or surfaces, with tortuous features, are not effectively coated.

Supercritical chemical fluid deposition (hereafter, "SFD") is one conventional solution that is capable of depositing a metal coating onto a complicated surface/feature structure. During a SFD process, a supercritical fluid (substances at a temperature and pressure above a critical point (in a phase diagram) such that distinct gas and liquid phases do not exist), also referred to as the working fluid, is used as a solvent to the organometallic precursor. There are many supercritical fluids available for SFD process, but the most convenient may be carbon dioxide. The liquid-like state of the supercritical fluid enables increased solubility of the organometallic precursor, and the gas-like state of the supercritical fluid enables a deep, conformal penetration of the features of the substrate.

SFD processes have conventionally been performed in a hot-wall processing system 10, an example of which is shown in FIG. 1. The hot-wall processing system 10 includes a processing chamber 12 enclosing a processing space 14 that is heated externally. A substrate 16 and an organometallic precursor 18 are added to the processing chamber 12 and sealed. A working fluid (represented by arrows 20) is added, for example, via an injection system 22, and the processing space 14 is heated until the temperature and pressure required for the supercritical state of the working fluid is exceeded. The organometallic precursor 18 dissolves in the supercritical working fluid within the process space 14. A reducing agent, usually hydrogen, is then introduced to cause the metal portion of the organometallic precursor 18 to deposit onto the substrate 16. However, the metal portion is also deposited on other, interior surfaces of the processing chamber 12.

While the hot-wall processing system 10 of FIG. 1 is effective at coating substrates 16, the process is wasteful in that it deposits metal on all surfaces within the processing chamber 12. An alternative to the hot-wall processing system 10 is a cold-wall processing system 30, which is shown in FIG. 2. The cold-wall processing system 30 places a substrate 32 on a heated pedestal 34 within the processing space 36 of the processing chamber 38. With the substrate 32 and an organometallic precursor 40 in place, the processing chamber 38 is sealed and evacuated. A working fluid (represented by arrows 42) is added, for example, via an injection system 44, and the processing chamber 38 is heated until the supercritical state of the working fluid is surpassed. The organometallic precursor 40 dissolves in the supercritical working fluid, and then the reducing agent (again, usually hydrogen) is added. To prevent deposition of the metal component onto all interior surfaces of the chamber 38 (like the aforementioned hot-wall processing system 10 (FIG. 1)), the organometallic precursor 40 should be thermally stable, stable to hydrogen reduction at lower temperature, and yet able to be reduced at elevated temperatures. The pedestal 34 of the cold-wall processing system 30 is heated such that deposition of the metallic portion is on the substrate and pedestal. Thus, the cold-wall processing system is more efficient than the hot-wall process 10 (FIG. 1), and is particularly useful for depositing copper and ruthenium coatings.

Backfluorinated NHC carbene complexes, such as those having been described in U.S. application Ser. No. 13/927,295 (being incorporated herein by reference, in its entirety) have proven useful in overcoming the foregoing issues with respect to the deposition of noble metals; however, the need for improvement remains. Particularly, there remains a need for more efficient synthesis methods by which bulk quantities of backfluorinated NHC carbene complexes may be prepared for industrial use. Moreover, there remains a need for mechanisms of synthesis that enable additional functionalization of the NHC carbene complexes.

SUMMARY OF THE INVENTION

The present invention overcomes the foregoing problems and other shortcomings, drawbacks, and challenges associated with the synthesis of NHC carbene complexes. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention a method of synthesizing a backfunctionalized imidazolinium salt comprises the formula:

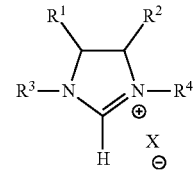

In the formula, $R^1$ is selected from the group consisting of an ester group, an amide group, and an aromatic group; $R^2$ is selected from the group consisting of hydrogen, an ester group, an amide group, and an aromatic group; $R^3$ and $R^4$ are each an aliphatic group; and X is an anion. The method comprises cyclization of a halogenated acrylate with Hünig's base in a solvent.

In accordance with other embodiments of the present invention, a method of synthesizing a backfunctionalized imidazolinium salt comprises cyclization of a halogenated acrylate with Hünig's base in a solvent.

Still other embodiments of the present invention are directed to backfunctionalized imidazolinium salts comprising the formula:

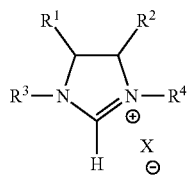

In the formula, $R^1$ is selected from the group consisting of an ester group, an amide group, and an aromatic group; $R^2$ is selected from the group consisting of hydrogen, an ester group, an amide group, and an aromatic group; $R^3$ and $R^4$ are each an aliphatic group; and X is an anion.

According to other embodiments of the present invention, a backfunctionalized imidazolinium salt comprises the formula:

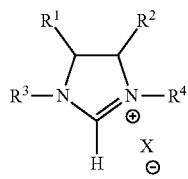

In the formula, $R^1$ is selected from the group consisting of an ester group, an amide group, and an aromatic group; $R^2$ is selected from the group consisting of hydrogen, an ester group, an amide group, and an aromatic group; each of $R^3$ and $R^4$ being separately selected from the group consisting of a $C_1$-$C_{20}$ alkyl group, $C_1$-$C_{20}$ partially fluorinated alkyl group, an aryl group, an aryl group with para $CF_3$ functionality, an aryl group having $C_1$-$C_{20}$ partially fluorinated alkyl groups or partially fluorinated alkoxy groups, and a $C_1$-$C_{20}$ partially fluorinated aliphatic group, and a $C_1$-$C_{20}$ aryl group; and X is an anion.

In still other embodiments of the present invention, a backfunctionalized imidazolinium salt selected from the group of formulae consisting of:

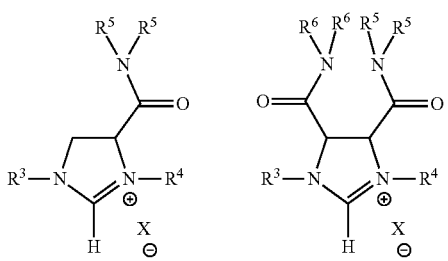

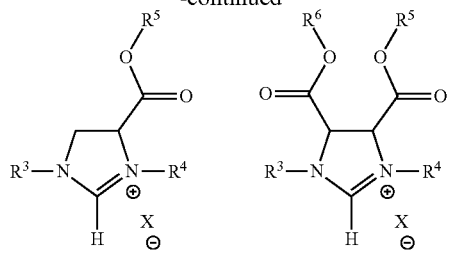

In the formula, $R^1$ is selected from the group consisting of an ester group, an amide group, and an aromatic group; $R^2$ is selected from the group consisting of hydrogen, an ester group, an amide group, and an aromatic group; each of $R^3$ and $R^4$ being separately selected from the group consisting of a $C_1$-$C_{20}$ alkyl group, $C_1$-$C_{20}$ partially fluorinated alkyl group, an aryl group, an aryl group with para $CF_3$ functionality, an aryl group having $C_1$-$C_{20}$ partially fluorinated alkyl groups or partially fluorinated alkoxy groups, and a $C_1$-$C_{20}$ partially fluorinated aliphatic group, and a $C_1$-$C_{20}$ aryl group; each of $R^5$ and $R^6$ being separately selected from the group consisting of a partially fluorinated alkyl group, a fluorinated aryl group, an aliphatic group, and an aryl group; and X is an anion.

Still other embodiments of the present invention are directed to backfunctionalized imidazolinium salt selected from the group of formulae consisting of:

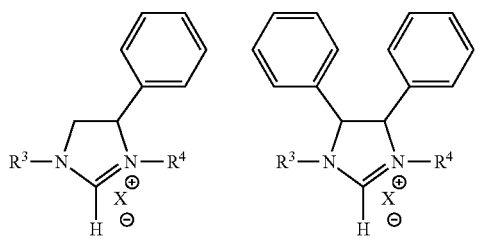

In the formula, each of $R^3$ and $R^4$ being separately selected from the group consisting of a $C_1$-$C_{20}$ fluorinated alkyl group, a $C_1$-$C_{20}$ fluorinated aryl group, a $C_1$-$C_{20}$ fluorinated aliphatic group, and a $C_1$-$C_{20}$ aryl group; and X is an anion.

Yet other embodiments of the present invention are directed to ionic liquids of the formula:

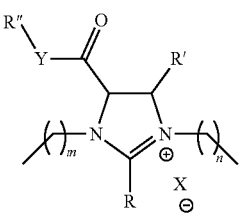

In the formula, R is a hydrogen or a methyl group; R' is selected from the group consisting of hydrogen, an ester group, an amide group, and an aromatic group; R" is selected from the group consisting of an alkyl group and an aromatic group; the subscript m may range from 0 to 10; the subscript n may range from 0 to 10; X is a halide or an anion; and Y is oxygen, sulfur, or NR".

According to embodiments of the present invention, a method of synthesizing a backfluorinated imidazolinium salt includes cyclization of a halogenated, fluorinated allyl ether with Hünig's base in polar aprotic solvent.

Other embodiments of the present invention are directed to methods of synthesizing backfluorinated second generation Grubbs' and Grubbs-Hoveyda catalysts. The methods include reacting a backfluorinated NHC carbene with a first generation Grubbs' and Grubbs-Hoveyda catalyst.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
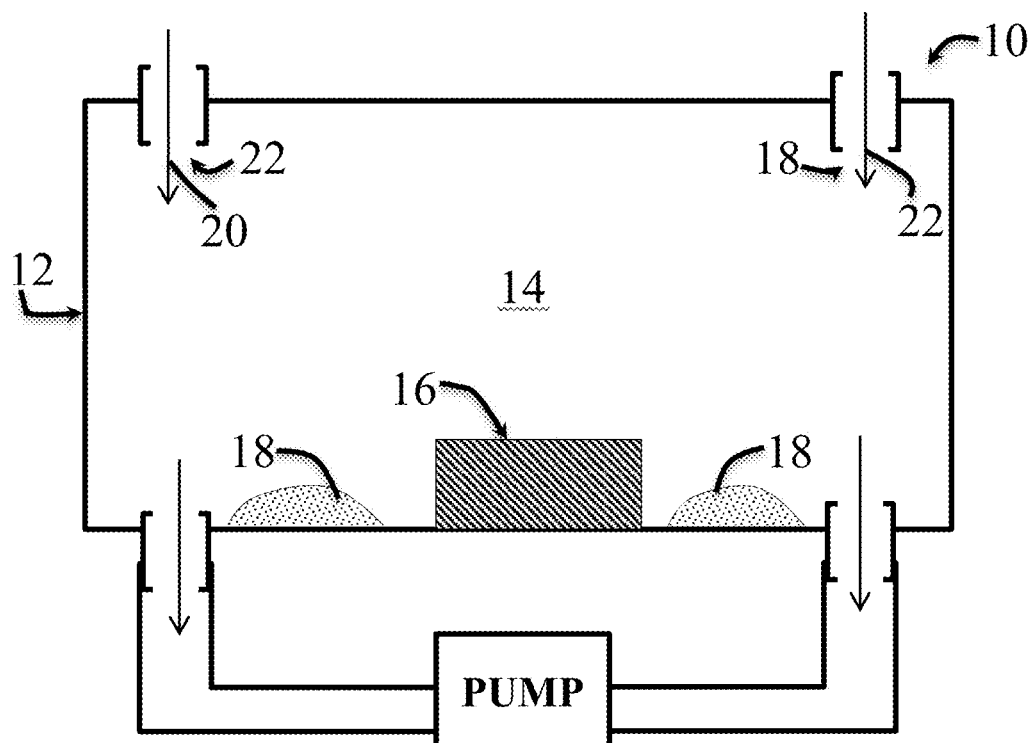
FIG. 1 is a schematic representation of a conventional, hot-wall processing system suitable for supercritical chemical fluid deposition processes.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Backfunctionalized imidazolinium salts according to embodiments of the present invention include a general structure of:

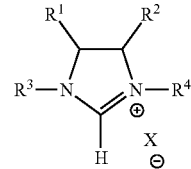

(hereafter referred to as "backfunctionalized imidazolinium") wherein $R^1$ is selected from the group consisting of an ester group, an amide group, and an aromatic group, $R^2$ is selected from the group consisting of hydrogen, an ester group, an amide group, and an aromatic group, and $R^3$ and $R^4$ are each separately selected from the group consisting a $C_1$-$C_{20}$ alkyl group, $C_1$-$C_{20}$ partially fluorinated alkyl group, an aryl group, an aryl group with para $CF_3$ functionality, an aryl group having $C_1$-$C_{20}$ partially fluorinated alkyl groups or partially fluorinated alkyoxy groups, and a $C_1$-$C_{20}$ partially fluorinated aliphatic group, and a $C_1$-$C_{20}$ aryl group (with the proviso that some partially fluorinated alkyl groups may require longer buffer). X, in the illustrated structure, is a halogen. Functional groups of $R^1$ and $R^2$ may be in either a cis- or trans-configuration, as provided in greater detail below.

As used herein, "partially fluorinated" is a perfluoroalkyl group having a 1-3 carbon methylene buffer attached by either a carbon [perfluoroctyl(ethyl)-] or an oxygen [perfluoroctyl(ethoxy)-] to an aromatic ring.

As used herein, "olefin metathesis" is an organic reaction in which fragments of alkenes are redistributed by scission and regeneration of carbon-carbon double bonds.

As used herein, "functionalized" refers to an ester, amide, or aromatic functionality.

"Backfunctionalized" refers to an ester, amide, or aromatic functionality that is attached to the 4 position, 5 position, or both of the imidazolinium ring.

According to more specific embodiments of the present invention, backfunctionalized imidazolinium salts may be selected from the group of structures consisting of:

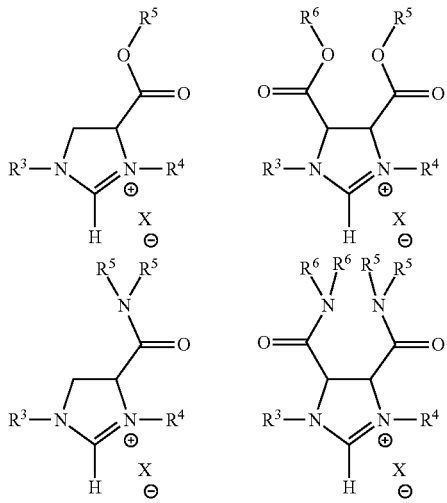

where $R^1$, $R^2$, $R^3$, $R^4$, and X are as described above and $R^5$ and $R^6$ are each separately selected from a fluorinated alkyl group, a fluorinated aryl group, an aliphatic group, and an aryl group. The mono- and di-ester embodiments may be extremely versatile and, as one of ordinary skill in the art having the benefit of this disclosure would appreciate, could accommodate a wide variety of functional groups at $R^1$-$R^4$.

Still further embodiments of the present invention include backfunctionalized imidazolinium salts selected from the group consisting of:

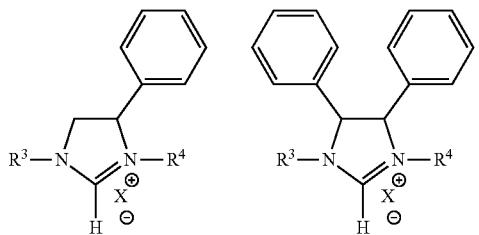

Backfunctionalized NHC carbenes according to embodiments of the present invention may be coordinated in metal complexes, wherein the metal is selected from the group consisting of rhenium, ruthenium, osmium, rhodium, iridium, palladium, platinum, silver, and gold. Furthermore, inorganic complexes for coordination with backfunctionalized NHC carbenes according to embodiments of the present invention may include acetylacetonate, alkoxy, alkyl, aryl, aryloxy, carbonyl, halide, imido, oxo, pyridine, trialkylphosphine, and triarylphosphine.

Figures 3, 4:
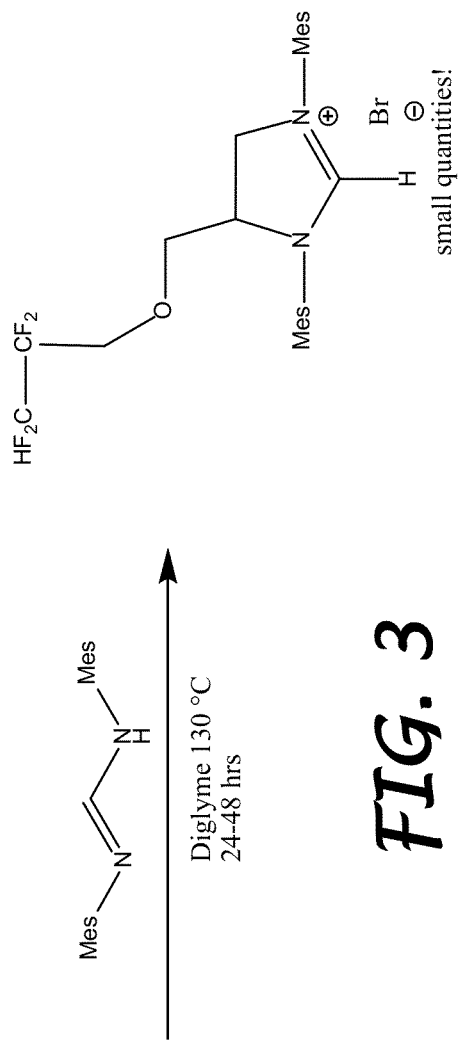
FIG. 3 is an illustrative representation of a formamidine cyclization of halogenated tetrafluoropropyl allyl ether in diglyme in the presence of formamidine base and according to an embodiment of the present invention.
FIG. 4 is an illustrative representation of a formamidine cyclization of halogenated tetrafluoropropyl allyl ether in diglyme in the presence of N,N-diisopropylethylamine base according to another embodiment of the present invention.

Referring now to the figures, and in particular to FIG. 3, synthesis of backfluorinated N-heterocyclic ("NHC") carbenes, and more particularly synthesis of backfluorinated imidazolinium salts which may be deprotonated to form free backfunctionalized NHC carbenes, according to an embodiment of the present invention is shown. Generally, synthesis includes formamidine cyclization in a polar aprotic solvent. Suitable polar aprotic solvents may include, but are not limited to ethylene glycol dimethyl ether (glyme), diethylene glycol dimethyl ether (diglyme), and triethylene glycol dimethyl ether (triglyme). In the particularly illustrative embodiment of FIG. 3, formamidine cyclization of brominated tetrafluoropropyl allyl ether and mesityl formamidine in diglyme (the selected polar aprotic solvent) in the presence of mesityl formamidine as the base is shown.

A similar embodiment of formamidine cyclization is shown in FIG. 4, but uses N,N-diisopropylethylamine (commonly referred to as "Hünig's base") as the base.

Figure 5:
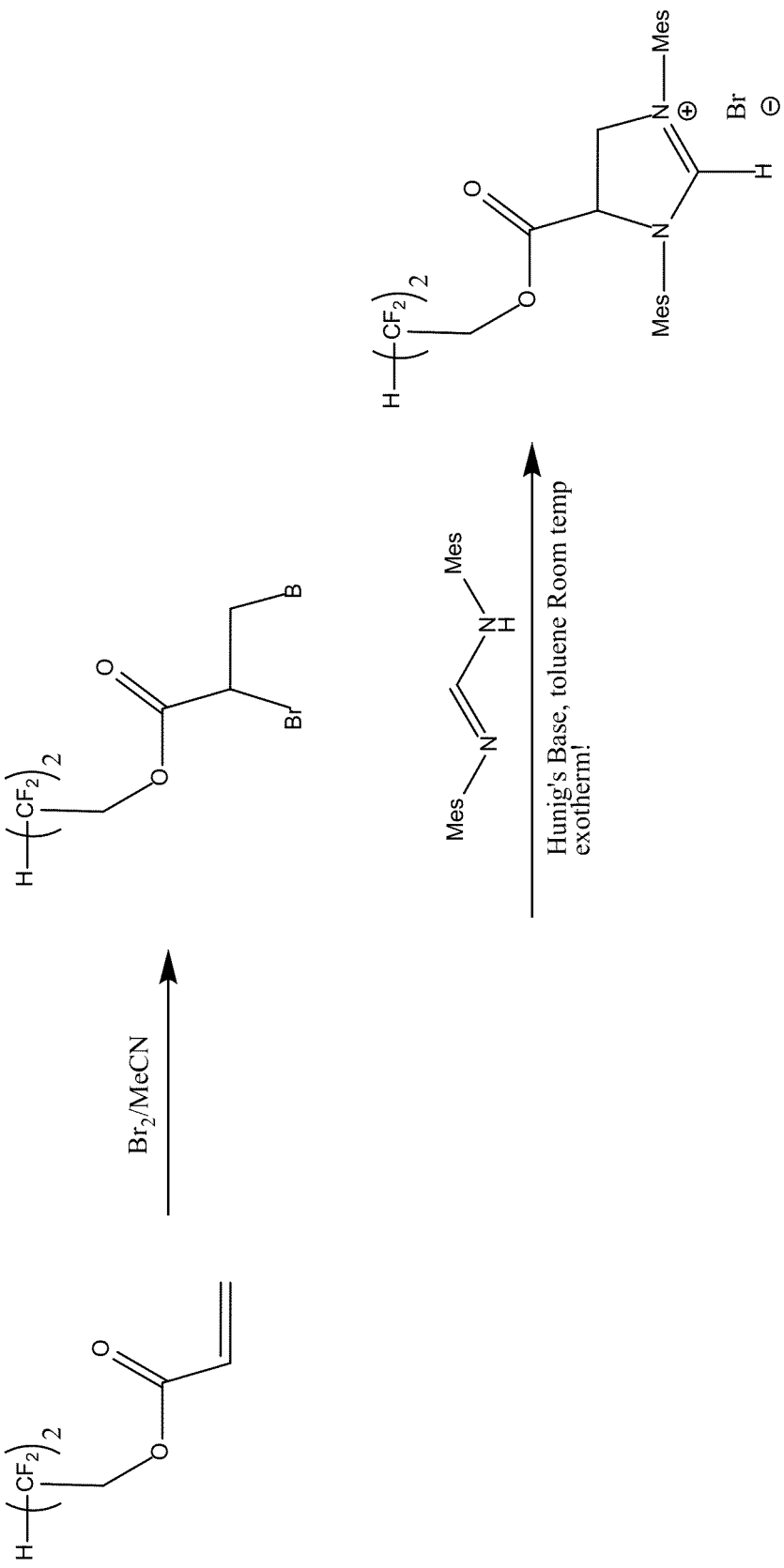
FIG. 5 is an illustrative representation of formamidine cyclization of a halogenated, fluorinated acrylate in toluene in the presence of Hünig's base and according to an embodiment of the present invention is shown.

Referring now to FIG. 5, formamidine cyclization of a halogenated, fluorinated acrylate (specifically illustrated as tetrafluoropropyl acrylate) is shown in accordance with an embodiment of the present invention. Although not necessary, the halogenated, fluorinated acrylate may first be synthesized from a fluorinated acrylate, which is also included in the illustration of FIG. 5. A variety of fluorinated acrylates, such as perfluorooctyl-ethyl acrylate, and higher homologs based on tetrafluoropropanol, such as 1H,1H,9H-perfluorononanol may additionally or alternatively be used. Various aliphatic and aromatic esters and amides may additionally or alternatively be used. Formamidine cyclization according to this embodiment, carried out in toluene in the presence of Hünig's base, is an exothermic reaction and does not require heating. Still other bases may be used in synthesis of imidazolinium salts according to embodiments of the present invention, such as triethylamine and pyridine, may be used. It is believed that conventional methods have been unsuccessful in using such bases because the elevated temperatures required to complete the cyclization (temperatures in excess of 100° C.). Such bases are too nucleophilic at elevated temperatures and thus the less nucleophilic Hünig's base or aromatic formamidine was used. Because the synthesis methods according to embodiments of the present invention occur at temperatures that are lower than the conventional methods, such alternative bases become viable options. Moreover, cost savings via these alternative bases may increase productivity while minimizing costs.

Figure 6:
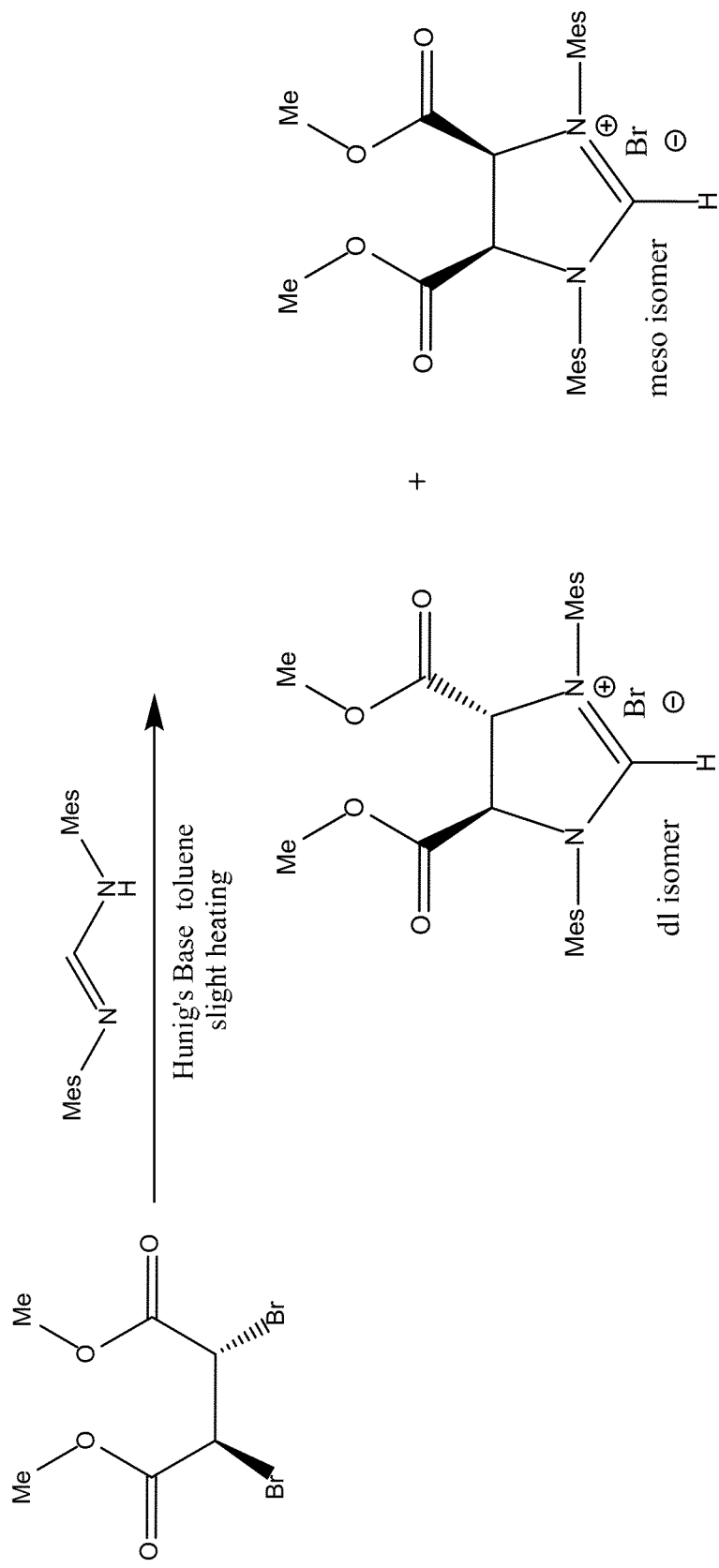
FIG. 6 is an illustrative representation of formamidine cyclization of a halogenated maleate in toluene in the presence of Hünig's base and in accordance with an embodiment of the present invention.

In still other embodiments, such as the embodiment shown in FIG. 6, formamidine cyclization of a halogenated maleate (specifically illustrated as brominated dimethyl maleate) may be carried out in toluene in the presence of Hünig's base at low heat (temperatures being less than about 60° C.). While not wishing to be bound by theory, it is believed that formamidine cyclization proceeds firstly, by a standard bromination mechanism where bromine attacks the double bond and forms cyclic bromonium cation. The resulting bromide anion attacks one of the carbons from the back resulting in the d,l dibromide.

While not specifically illustrated, embodiments of formamidine cyclization of other olefin based ester compounds (such as fumarate) may proceed in manner similar to those embodiments illustrated in FIGS. 5 and 6; however, it may be necessary, in such embodiments, to further heat the reaction during cyclization because of steric hindrance.

Besides the mesityl formamidine complex, as shown herein, additional formamidine complexes are possible according to other embodiments. Generally, such embodiments may include, but are not limited to aromatic formamidine complexes (such as, o-tolyl-formamidine, p-tolyl-formamidine, and 2,6-diisopropylphenyl-formamidine), fluorinated formamidine complexes (such as, 4-CF$_3$-phenyl-formamidine) and aliphatic formamidine complexes (such as, adamantyl-formamidine, cyclohexyl-formamidine, and 2-ethyl-1-hexyl-formamidine). Such imidazolinium salts may be synthesized using a solvent (such as toluene or acetone) with a base (such as Hünig's base, triethylamine, or, in some embodiments, formamidine) with moderate heating (less than about 60° C., or more preferably, about 40° C.) for a period of time (less than about 12 hours, or more preferably, about 4 hours); however, the temperature, reaction time, or both may depend on an amount of steric hindrance (such as in reactions using adamantyl-formamidine and 2,6-diisopropylphenyl-formamidine).

These embodiments of the present invention demonstrate a significant benefit over conventional synthesis methods, which were traditionally limited to aromatic side chains (R$^3$ and R$^4$ groups) and such methods not necessarily applied to aliphatic groups.

Figure 7:
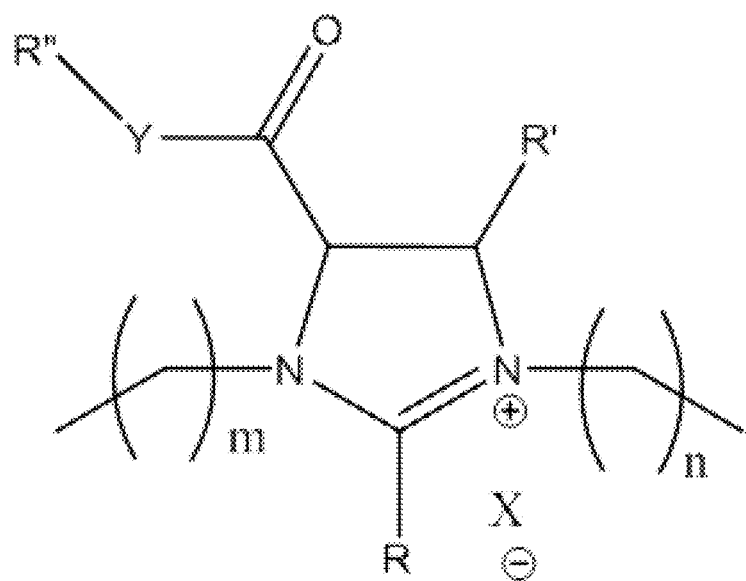
FIG. 7 is an illustrative representation ionic liquid according to an embodiment of the present invention.
Figure 8:
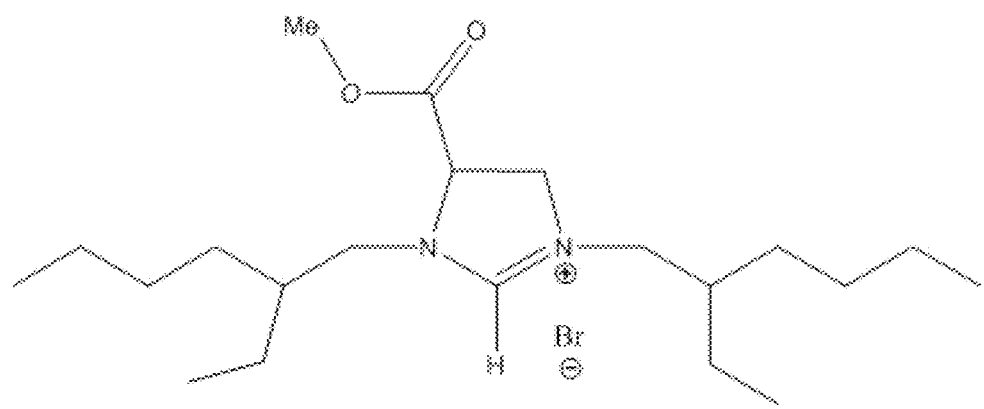
FIG. 8 is representation of 2-ethylhexyl imidazolinium salt, an ionic liquid according to an embodiment of the present invention.

Synthesis methods, as described herein, may in some embodiments yield a new class of imidazolinium salts that behave as ionic liquids. FIG. 7 illustrates, generally, a structure for such an ionic liquid, wherein subscripts m and n may each range from 0 to 10 and the subscript m is selected independently of the subscript n. X in FIG. 7 may be a halide or another anion; R may be hydrogen or a methyl group; R' may be hydrogen, an ester group, or an amide group; R" may be an alkyl group or an aromatic group; Y may be oxygen, sulfur, or NR". Ionic liquids are salts that have a melting point of less than about 100° C. One particular species of ionic liquid prepared in accordance with embodiments of the present invention is shown in FIG. 8 (2-ethylhexyl imidazolinium salt), and was synthesized by cyclization of 2-ethylhexyl formamidine and methyl 2,3-dibromopropionate (brominated methyl acrylate) using either Hünig's base or triethylamine as the base. The 2-ethylhexyl imidazolinium ionic liquid of FIG. 8 was soluble in a non-polar solvent (toluene) and is viscous oil at room temperature.

Ionic liquids, as described herein, may be useful as a plasticizer for advanced propellant formulations. Suitable propellant formulations may include, but are not limited to, ammonium perchorate-based propellants, ammonium dinitramide-based propellants, and furazan-based propellants. In accordance with other embodiments, the ionic liquids may be supported onto a surface such that two chains are extending away from the imidazolinium salt and approximately parallel to said surface.

Given the benefit of the disclosure herein, the skilled chemist would appreciated that formation of ionic liquids by cyclization according to embodiments of the present invention may include Hünig's base or other ones or combinations of bases as are provided herein.

One of the difficulties of conventional carbenes is the insolubility in scCO$_2$ at lower pressures (less than about 3000 PSI). While monofunctional imidazolinium salts, as prepared in accordance with embodiments discussed above, are potentially capable of supporting a perfluoroalkyl group with 24 fluorines (H(CF$_2$)$_{12}$CH$_2$O$^-$), economically speaking, only 16 or 17 fluorines (H(CF$_2$)$_8$CH$_2$O$^-$ and (F(CF$_2$)$_8$CH$_2$CH$_2$O$^-$) are feasible. An alternative would be to functionalize sides groups of the imidazolinium; however, such an option may present electronic risks. Alternatively still, functional groups could be added to a backside of the imidazolinium ring. In that regard, functionalization would lead to either performing a transamination (two perfluoroalkyl chains on the amine) or adding another ester linkage to the back of the ring. Adding a second ester group to the back of the ring is the more economical of the two choices.

Figure 9:
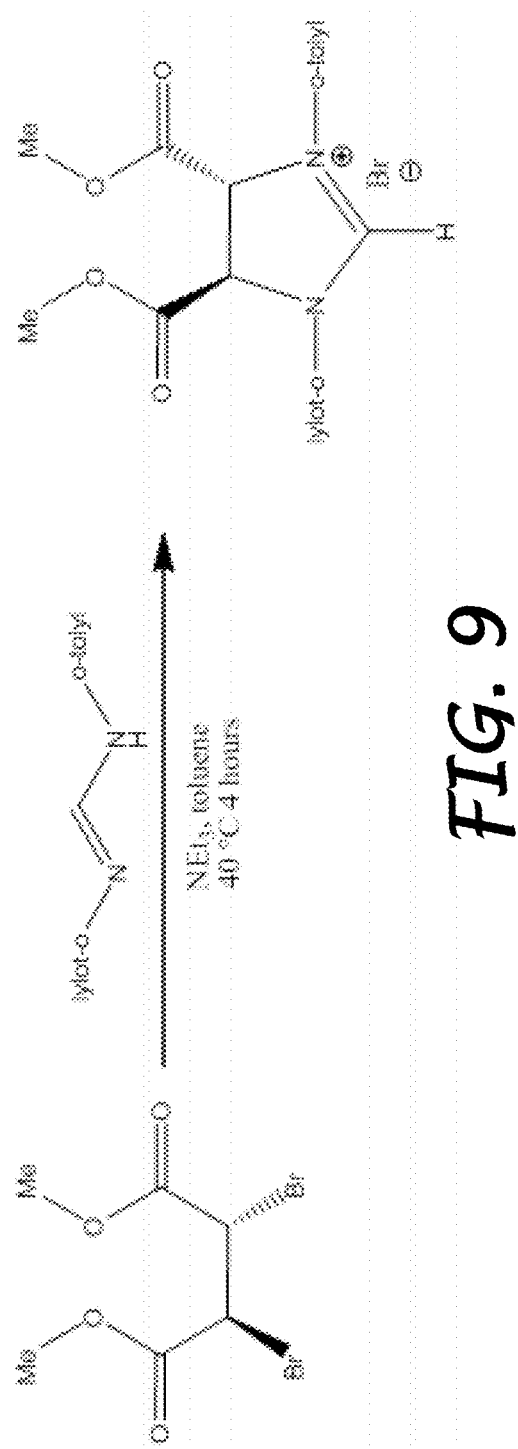
FIG. 9 is an illustrative representation of formamidine cyclization of a halogenated maleate in toluene in the presence of Hünig's base and in accordance with an embodiment of the present invention.
Figure 10:
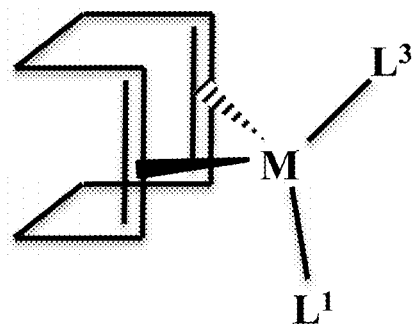
FIGS. 10-13 are illustrative representations of backfunctionalized NHC carbene-metal complexes in accordance with embodiments of the present invention.
Figure 11:
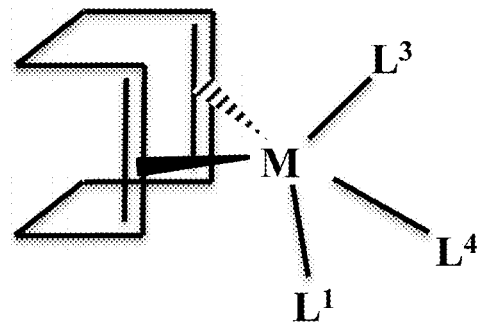
Figure 12:
Figure 13:
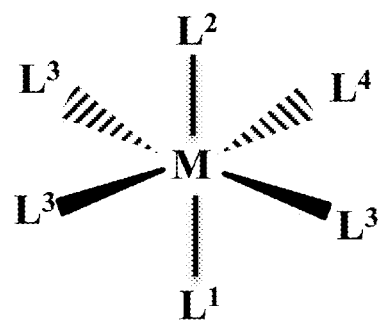

In referring again to FIG. 6, and again, while not wishing to be bound by theory, it is believed the cyclization reaction includes a meso product of a soluble halogen ion (rendered soluble by the Hünig's base cation), which displaces one of the halogens of the succinate. Heating the reaction at 60° C. for an extended period of time resulted in the observed meso product. The possibility of isomerization result may be reduced by limiting soluble halogens, which may be accomplished by the use of triethylamine and proceeding at a reduced temperature (for example, 40° C.). The resulting mechanism is shown in FIG. 9 and yields only one observed isomer.

Backfunctionalized imidazolinium salts according to embodiments of the present invention are not easily deprotonated the 2-proton by strong bases (such as potassium bis(trimethylsilyl)amide ("KHMDS") or potassium hydroxide) to yield a free NHC carbene for attachment to a metal center. Instead, to obtain a metal complex with the backfunctionalized imidazolinium salts described herein, such salts may be reacted with the imidazolinium salt with silver oxide to yield an NHC carbene/silver halide complex. This complex was then subsequently reacted with a metal complex to afford the NHC carbene/metal complex.

Using this method, embodiments of the backfunctionalized imidazolinium salts according to the present invention may be attached to a metal center, M, via first and second ligands, L$^1$ and L$^3$. Additional ligands, L$^2$, L$^3$ (if not NHC), and L$^4$ may be used to attach the metal center to yield a backfluorinated NHC carbene-metal complex. The third ligand, L$^2$ (or L$^3$) may be selected from the group consisting of an acetylacetonate, alkoxy, alkyl, aryl, aryloxy, carbonyl, halide, imido, oxo, pyridine, trialkylphosphine, or triarylphosphine; and the fourth ligand, L$^4$, may be selected from the group consisting of an acetylacetonate, alkoxy, alkyl, aryl, aryloxy, carbonyl, halide, imido, oxo, pyridine, trialkylphosphine, or triarylphosphine.

With reference now to FIGS. 10-13, four arrangements of the metal complex are shown. Generally, selection of the metal may depend on a particular application or use of the inorganic backfluorinated NHC carbene-metal complex. For example, in supercritical fluid deposition, M may be selected from the group consisting of rhenium, ruthenium, osmium, rhodium, iridium, palladium, platinum, silver, and gold; in catalysis processes, M may be selected from the group consisting of rhenium, ruthenium, osmium, cobalt, rhodium, iridium, nickel, palladium, platinum, copper, silver, and gold. More particularly, the metal of FIG. 10 may be selected from the group consisting of cobalt, iridium, and rhodium; the metal of FIG. 11 may be selected from the group consisting of nickel, palladium, and platinum; the metal of FIG. 12 may be selected from the group consisting of copper, silver, and gold; and the metal of FIG. 13 may be selected from the group consisting of rhenium, ruthenium, osmium, cobalt, rhodium, iridium, nickel, palladium, and platinum.

Figure 14:
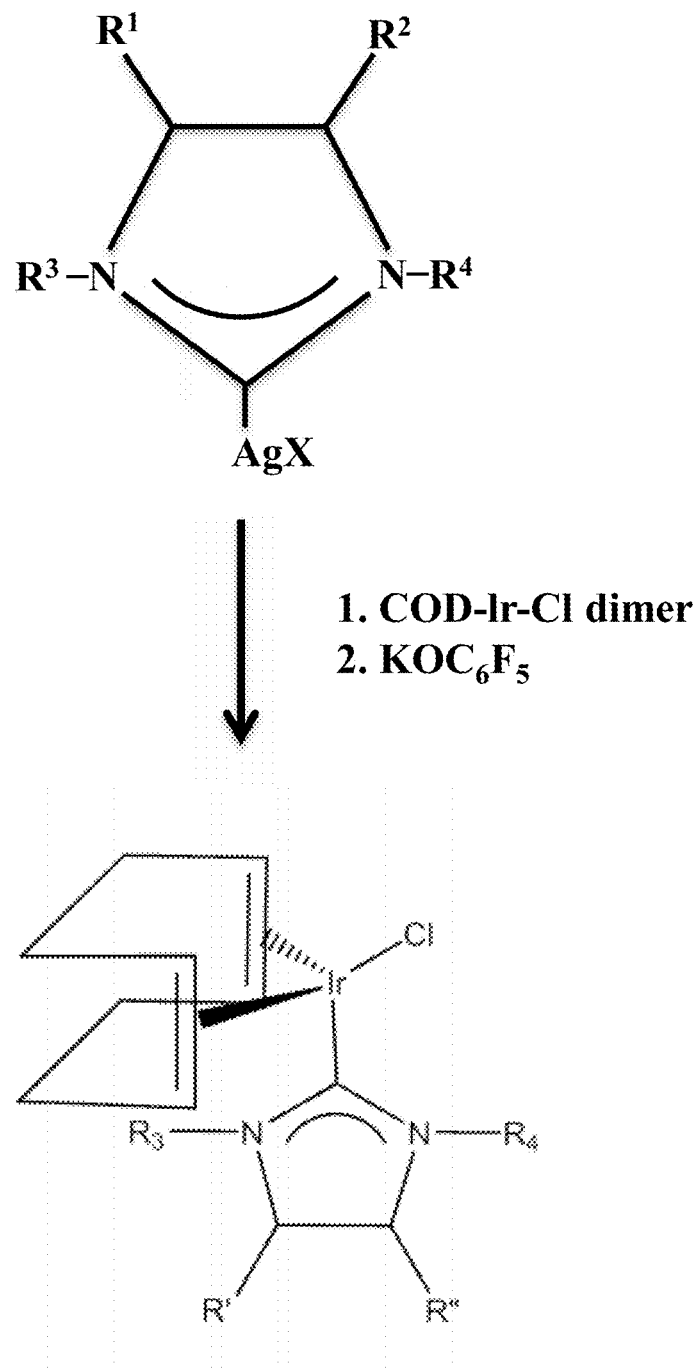
FIG. 14 is an illustrative representation of the synthesis of a backfunctionalized NHC carbene complex in accordance with an embodiment of the present invention.

Coordination of the metal to the carbene may be accomplished by adding a silver-NHC carbene complex to chloro-cyclooctadiene-iridium dimer, the latter of which is shown in FIG. 14.

Figure 15:
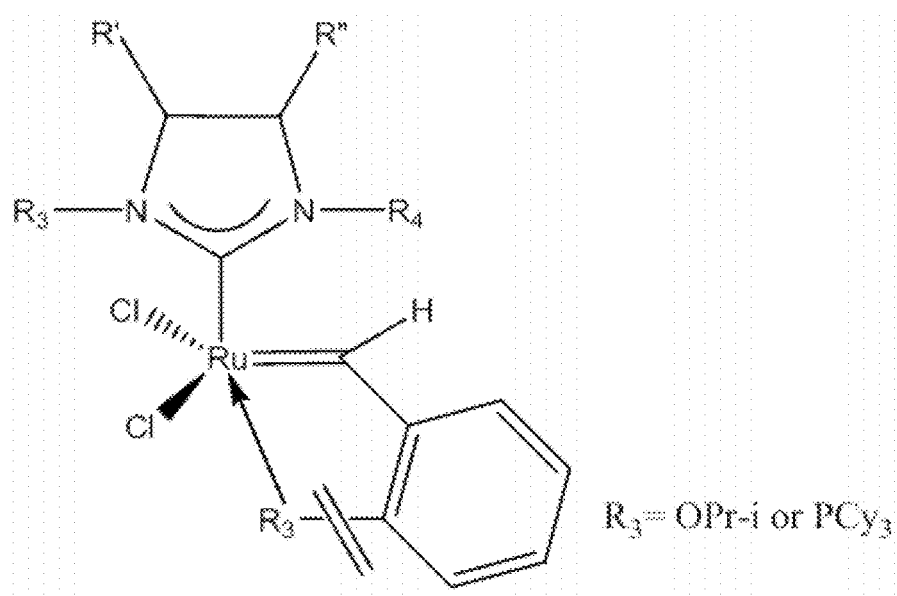
FIG. 15 is an illustrative representation of a backfunctionalized NHC carbene-metal complex in accordance with another embodiment of the present invention.

FIG. 15 illustrates ruthenium alkylidene system, which may be prepared in accordance with the method described herein by the addition of a silver-NHC carbene complex to the first Generation Grubbs or Grubbs-Hoveyda ruthenium alkylidene catalyst.

Reaction of conventional, backfluorinated NHC carbenes with first generation Grubbs' and Grubbs-Hoveyda catalyst gave backfluorinated second generation Grubbs' and Grubbs-Hoveyda catalysts. These catalysts were active for olefin metathesis and ring opening metathesis polymerization.

Imidazolinium salts, according to the various embodiments herein, may be used for a number of applications. For instance, such salts are especially suited for use as SCFD precursors. In the case of noble metals, the purpose of the backfluorinated NHC carbene-metal complex derived from the imidazolinium salts describe herein is to render the metal precursor soluble in supercritical solvent and stable to hydrogen at lower temperatures, and to be removed and deposit the metal onto the substrate at elevated temperatures.

Figure 2:
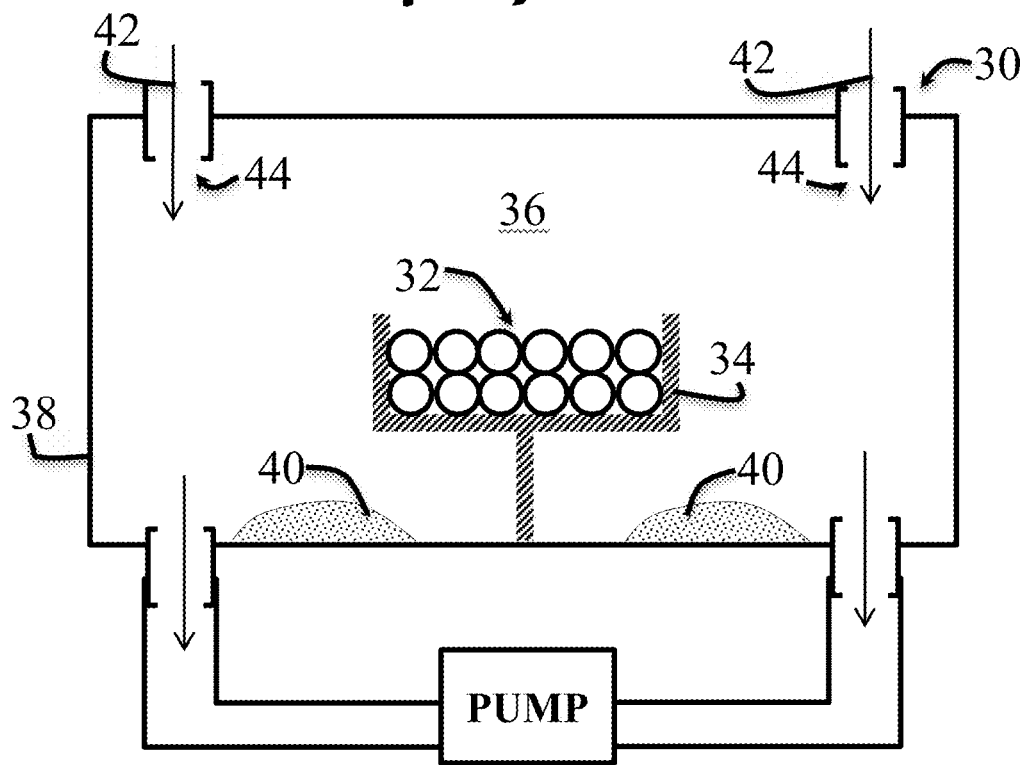
FIG. 2 is a schematic representation of a conventional, cold-wall processing system suitable for supercritical chemical fluid deposition processes.

The details of SCFD are provided in U.S. application Ser. No. 13/927,295; however, and briefly with reference now to FIGS. 2 and 16, a method of depositing metals using supercritical fluid deposition methods is described in accordance with one embodiment of the present invention. In using the cold-wall processing system 30 of FIG. 2, a noble metal may be deposited using SFD processing conditions according to an embodiment of the present invention illustrated in the flowchart of FIG. 16; however, the skilled artisan will readily appreciate that the illustrated cold wall reactor 30 layout should not be considered to be limiting. In the instant embodiment, the organometallic precursor 40 comprises a backfluorinated NHC carbene-metal complex according to at least one embodiment of the present invention.

Figure 16:
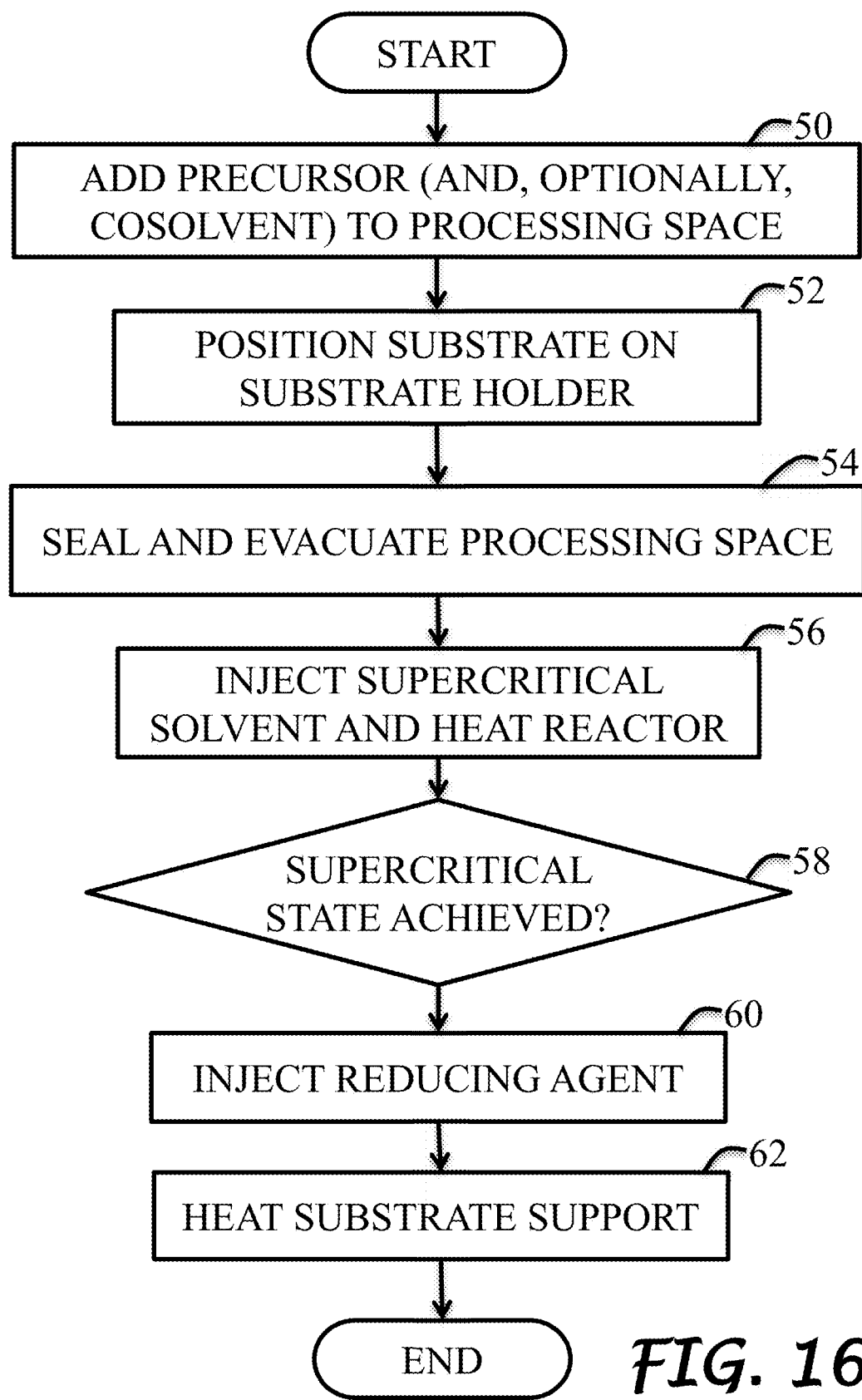
FIG. 16 is a flowchart illustrating a method of depositing metal on a substrate by cold wall supercritical chemical fluid deposition in accordance with an embodiment of the present invention.

In Block 50 of FIG. 16, a precursor 22 comprising a backfluorinated NHC carbene-metal complex, optionally with a cosolvent, is placed in the processing space 36. The substrate 32 is positioned on the substrate holder 34 (Block 52) and the processing space 36 is sealed and evacuated (Block 54).

A supercritical solvent, for example, carbon dioxide, may be injected via the injection system 44 and the chamber wall 38 may, optionally, be heated (Block 56). The reactor temperature depends on the selected supercritical solvent but, for exemplary purposes, may be 60° C. for carbon dioxide.

Once a supercritical state is achieved ("Yes" branch of Decision Block 58), the backfluorinated NHC carbene-metal complex precursor 40 begins to dissolve into the supercritical solvent, and a reducing agent may be injected via the injection system 44 (Block 60). Otherwise ("No" branch of Decision Block 58), the injection (Block 56) continues.

With the backfluorinated NHC carbene-metal complex precursor 40 dissolved, the substrate holder 34 may be heated to a desired temperature (Block 62). Because the substrate holder 34, and ultimately the substrate 32 are at an elevated temperature, deposition of the metal portion of the backfluorinated NHC carbene-metal complex precursor 40 from the supercritical solvent onto the substrate 32 may occur without deposition of metal portion onto chamber walls 38 or other components of the system 30.

With deposition complete, the system 30 may be cooled, the pressure relieved, and the substrate 32 removed.

According to another embodiment of use, the functional groups of such imidazolinium salts may be modified using transesterification. While alcohols are a primary group of interest, amines and sulfides may also be used to displace the ester group. Moreover, such methods of transesterification may be used for additional systems, described in detail below.

Figure 17A:
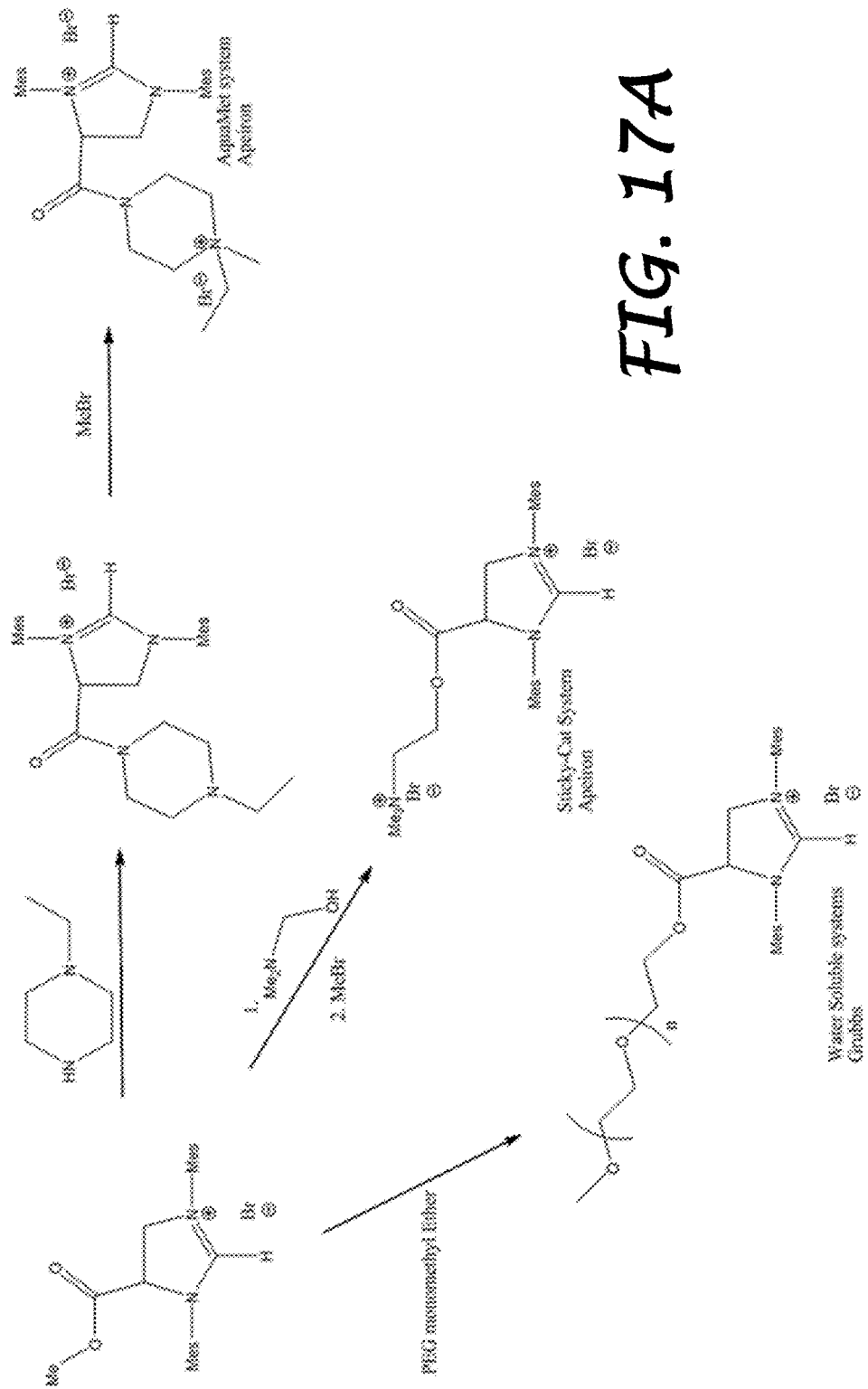
FIGS. 17A and 17B are illustrative representations of transesterification and/or transamination of backfunctionalized imidazolinium salts according to embodiments of the present invention.
Figure 17B:
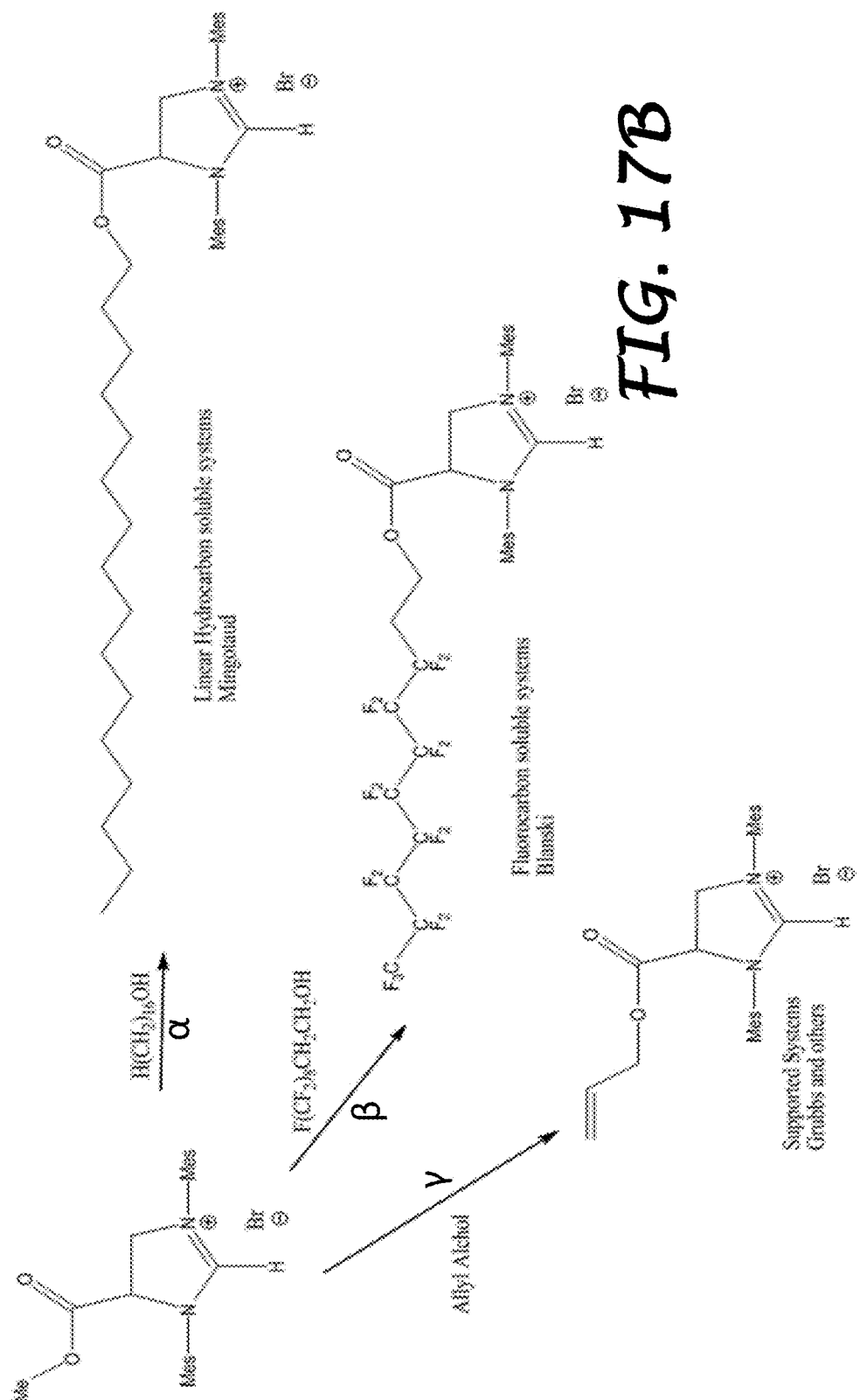

With reference now to FIGS. 17A and 17B, transesterification and/or transamination of backfunctionalized imidazolinium salts, according to the present invention, may afford catalysts that are conventionally difficult to manufacture. While the exemplary imidazolinium salts illustrated in FIGS. 17A and 17B are shown to include mesityl $R^3$ and $R^4$ groups, it would be readily appreciated by those of ordinary skill in the art having the benefit of the disclosure herein that other groups made be used. More particularly, three illustrative embodiments having fluorocarbon (pathway β of FIG. 17B), long chain hydrocarbon (pathway α of FIG. 17B), and allyl(pathway γ of FIG. 17B) backfunctionalized groups ($R^1$ with $R^2$=H) synthesized by an addition of the Grignard reagent to a diimine and reduction and cyclization to yield the imidazolinium salt. Such reactions may be carried out on a large scale with the proviso that the Grignard addition and the reduction steps are performed with care on larger scale.

Figure 18A:
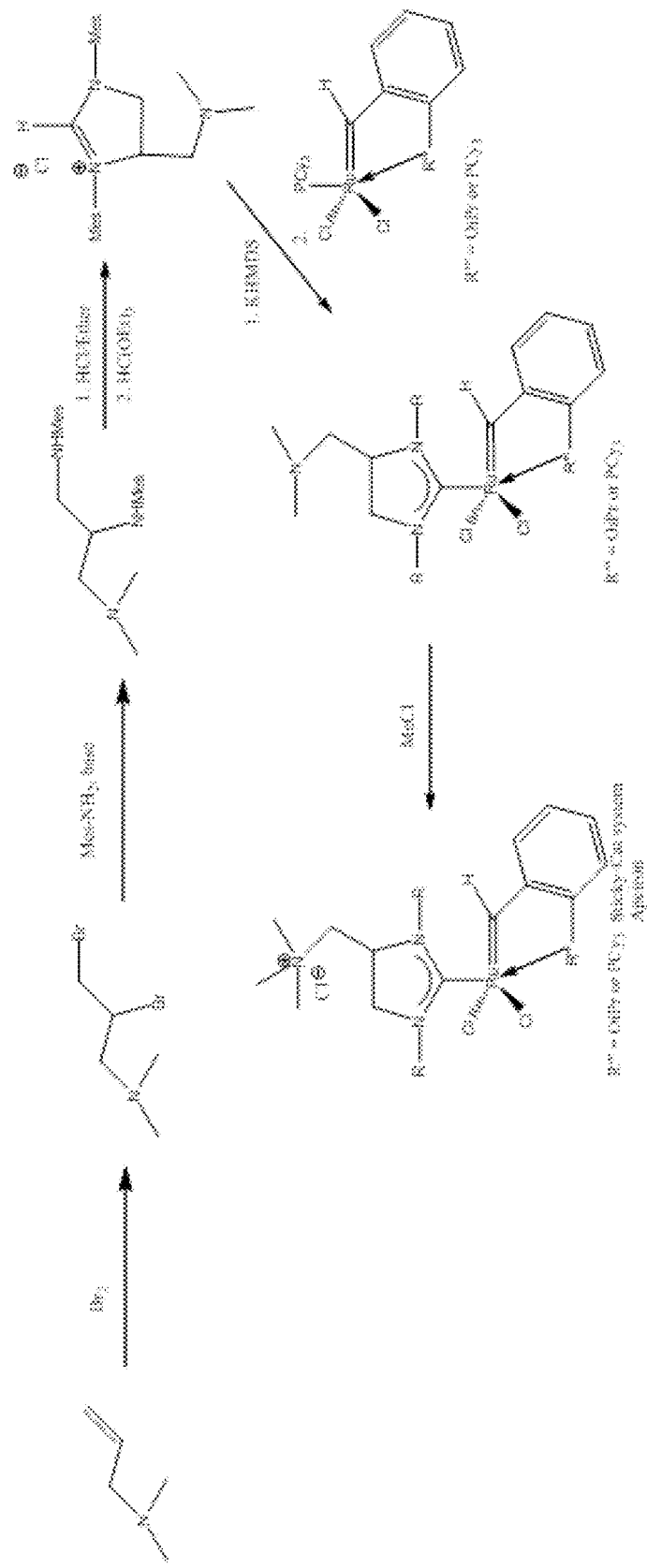
FIGS. 18A-19B are exemplary, illustrative representations for synthesizing Sticky-Cat catalyst-type systems (FIGS. 18A and 18B) and AquaMet catalyst-type systems (FIGS. 19A and 19B) in accordance with embodiments of the present invention.
Figure 18B:
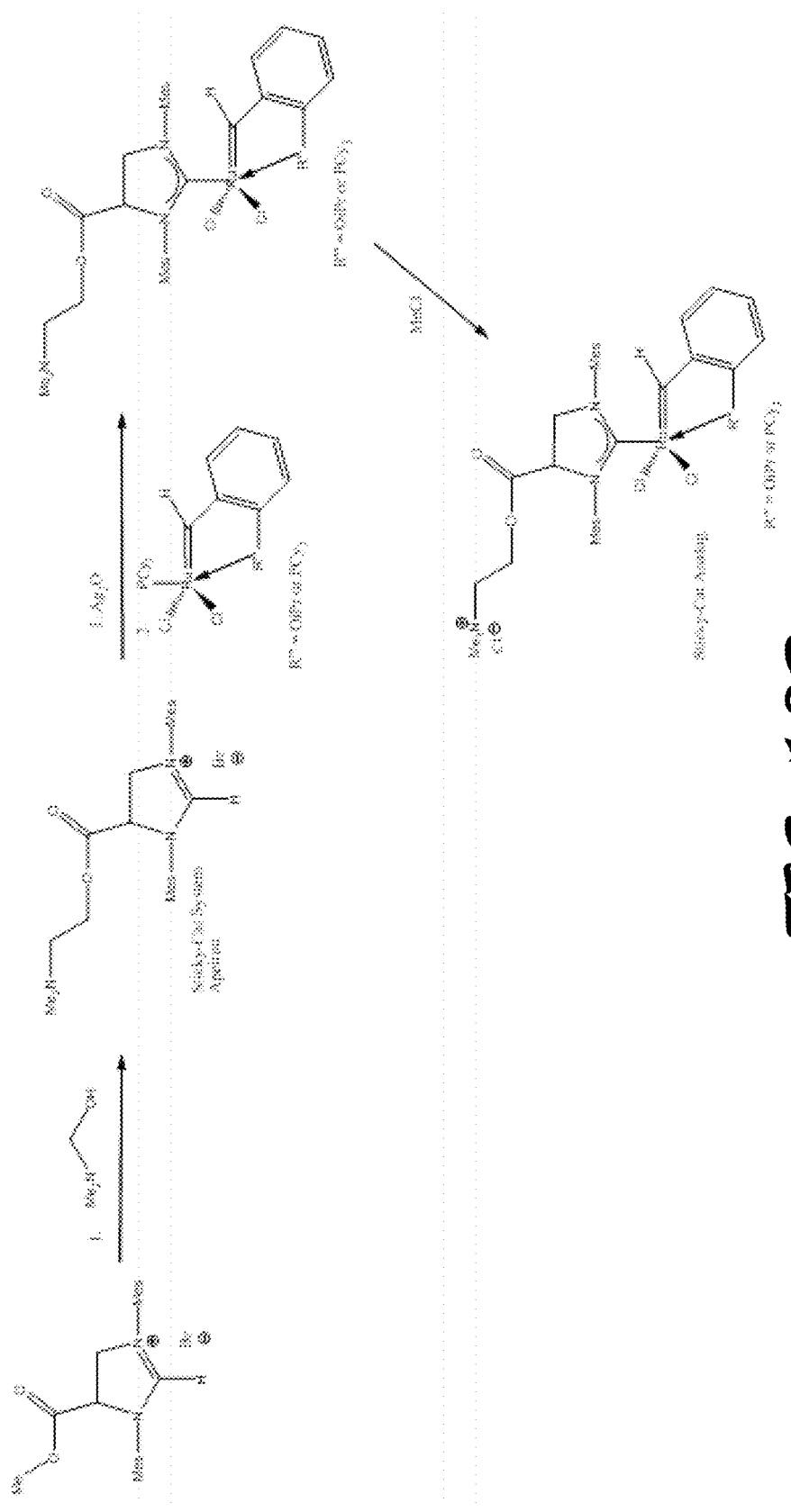
Figure 19A:
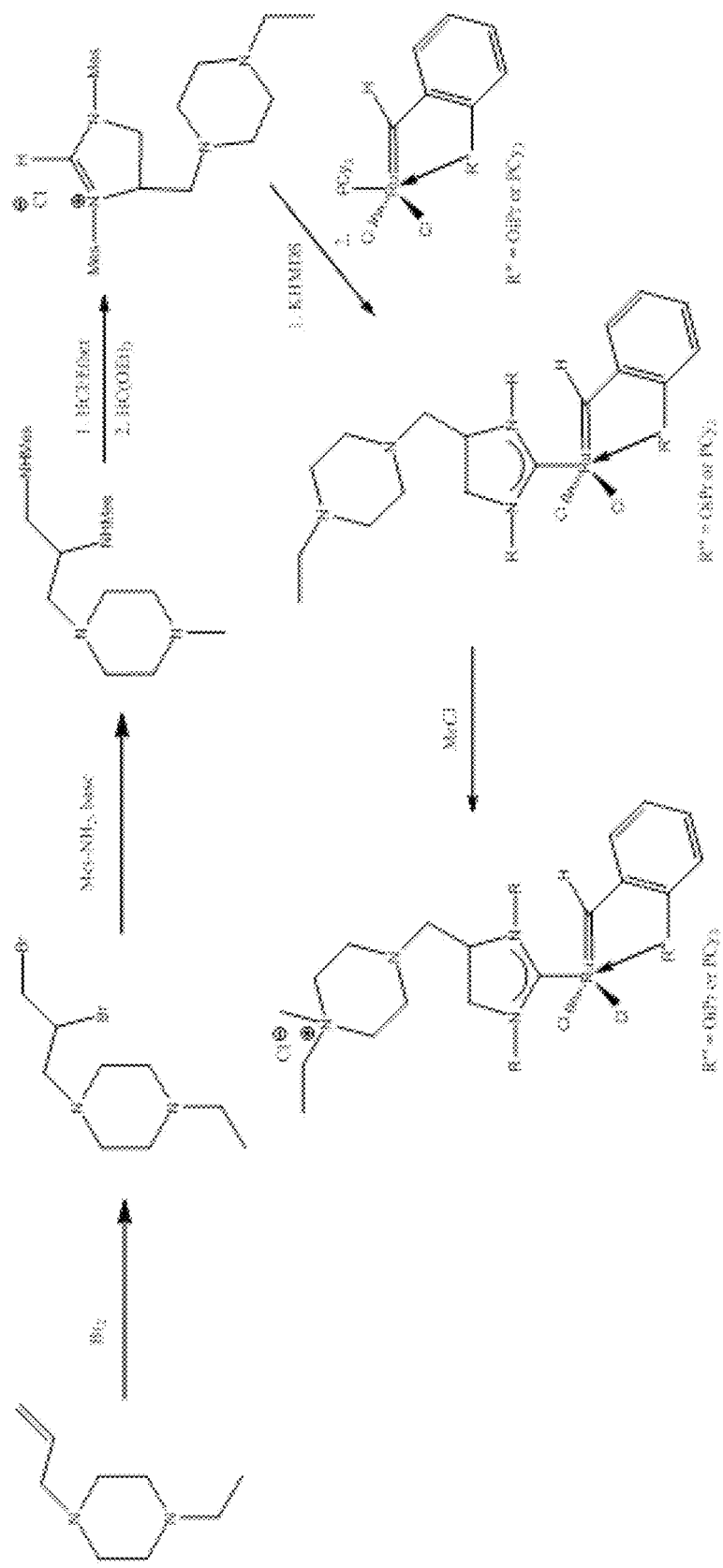
Figure 19B:
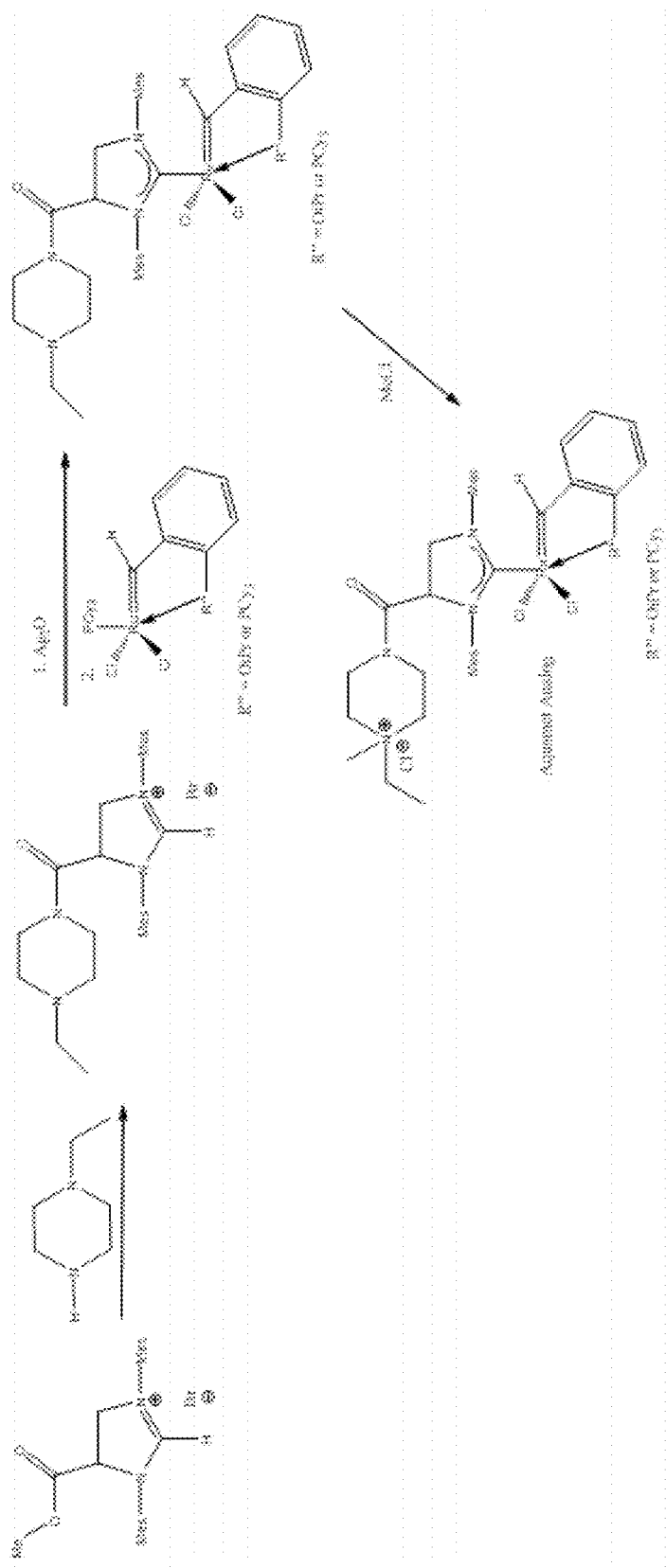

According to one exemplary embodiment, water soluble systems may be synthesized using the methods described herein by the transesterification of methyl ester imidazolinium salt with polyethylene glycol monomethyl ether. Conventionally, polyethylene glycol mesylate is added to 2-3-dimesityl-1-propanol and the product purified by column chromatography; however, such procedure is difficult to scale up. According to methods herein, the acid may be added and then cyclized with triethylorthoformate. In FIG. 18A, a "Sticky-cat" precursor is synthesized by bromination of N,N-dimethylamino-propene, followed by the addition of mesistylamine/base, and then cyclization by the addition of acid and triethylorthoformate cyclization. FIG. 19A illustrates an alternative embodiment wherein an "AquaMet" precursor is synthesized using a similar mechanism but for brominating allyl-methyl-piperazine. In FIGS. 18B and 19B, alternative potential pathways using transesterification are shown.

Figure 20:
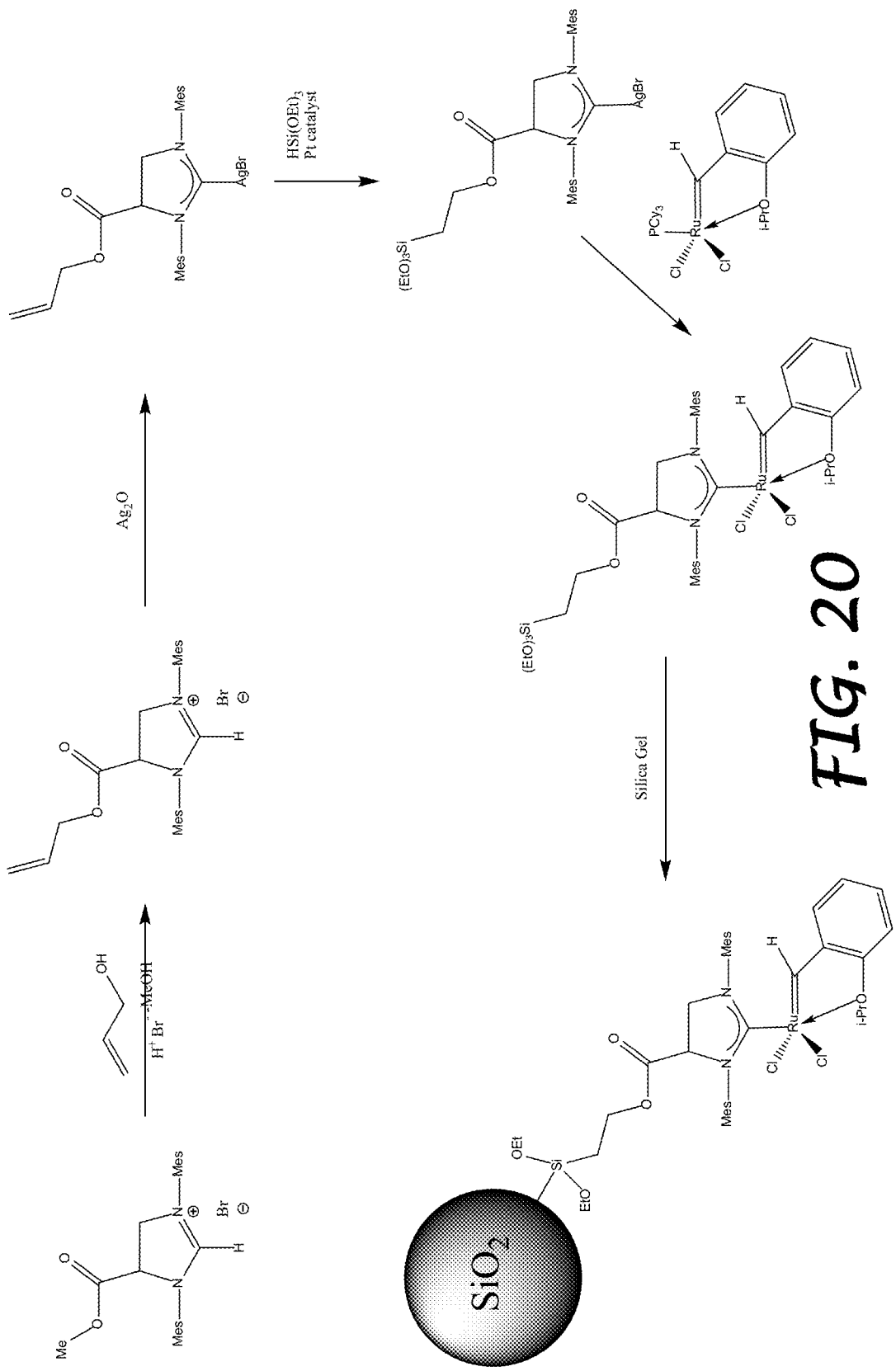
FIGS. 20 and 21 are exemplary, illustrative representations of methods of synthesizing silica-supported, backfunctionalized NHC carbene-metal complexes in accordance with two embodiments of the present invention.
Figure 21:
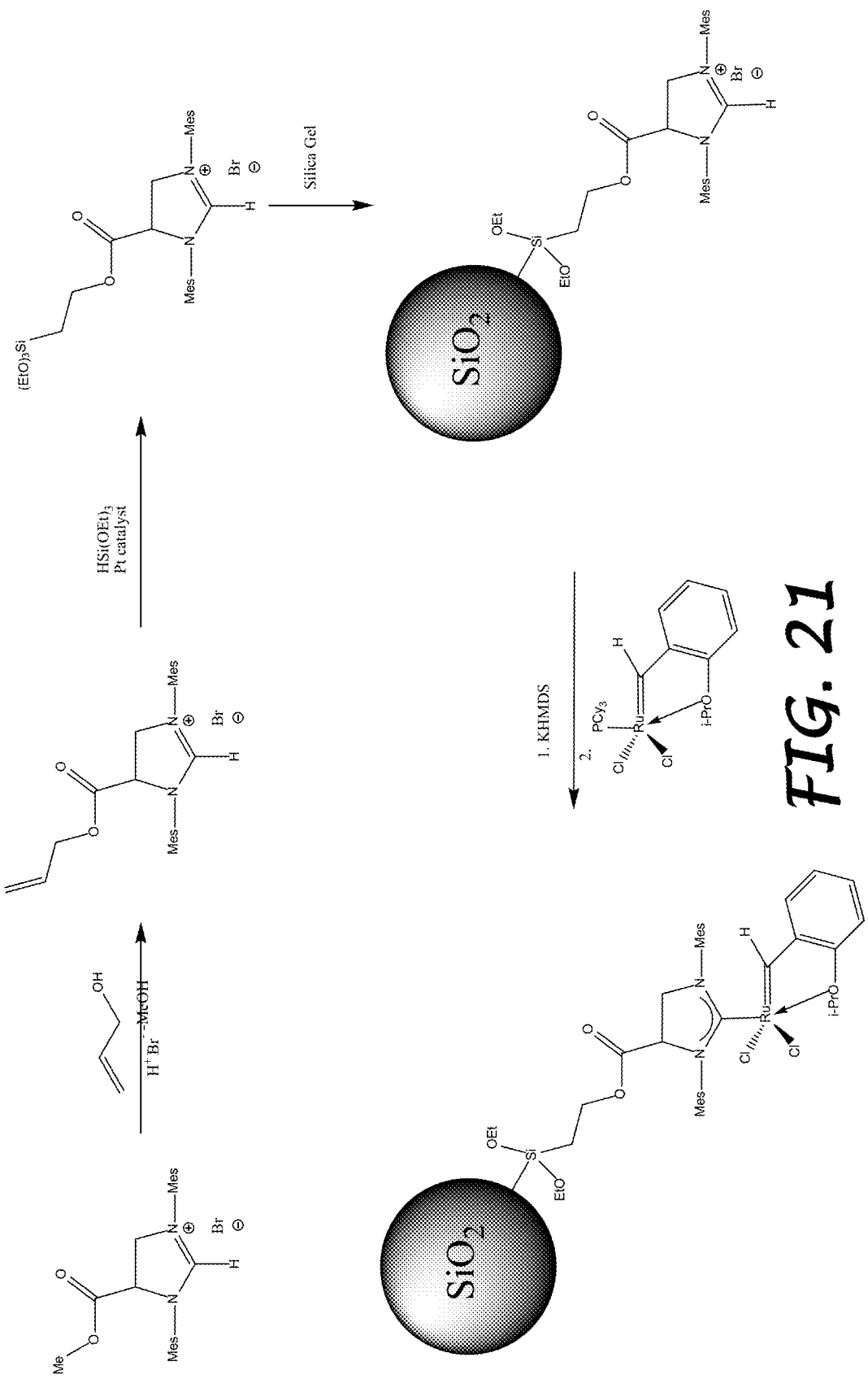

With references now to FIGS. 20-21, and in accordance with other embodiments of the present invention, the acrylate technology may be used for supported catalysts systems. For example, imidazolinium salts, as described herein, may, via transesterification, include a supported system. A suitable support system may include triethoxysilane as an anchor.

FIG. 20 illustrates an exemplary embodiment where a supported second Generation Grubb-Hoveyda catalyst is prepared.

FIG. 21 illustrates another exemplary embodiment that does not require silver transmetallation step. This methodology takes advantage of the lack of access to the α-proton to the ester. When an imidazolinium salt is in solution and homogenous, the addition of a strong base may preferentially deprotonate the α-proton while the 2-proton remains intact. Still, the 2-proton may be deprotonated and then the carbene may deprotonate the α-proton. In a supported system, access to the α-proton is limited to side access and any generated carbenes cannot deprotonate the α-proton due to site isolation. A bulky base such as KHMDS will be required.

While not particularly shown herein, backfluorinated NHC carbenes and backfluorinated NHC carbene-metal complexes according to various embodiment of the present invention may also be used within the field of catalysis. For example, backfluorinated NHC carbenes according to various embodiments of the present invention and as applied to transition metal catalyzed reactions afford new systems that are soluble in fluorinated solvents while retaining catalytic activity. More particularly, the disclosed backfluorinated NHC carbenes may be useful in biphase fluorous catalysis, wherein efficiency of a chemical reaction is increased by placing the active species in a fluorinated phase. Reactants, in a nonfluorinated phase, migrate into the fluorinated phase active species such that a chemical transformation takes place. The reactants may then migrate out of the fluorinated phase active species. Use of backfluorinated NHC carbene-metal complexes may increase efficient separation of product from the catalyst, particularly in system comprising fluorinated solvents or the reaction of olefins having a fluoroalkyl group.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example A—Imidazolinium Compounds from Acrylate and Maleate Systems

A scintillation vial was charged with a stir bar, mesityl formamidine (2.00 g, 7.13 mmol), toluene (8 g) and the tetrafluoropropyl 2,3-dibromopropionate (3.08 g, 8.92 mmol). The mixture is set stirring and a slight excess of Hünig's base (1.01 g, 7.84 mmol) is added. The reaction is exothermic and the solution goes clear. After a few minutes, the product and Hünig's base hydrobromide precipitate from solution. After stirring overnight, this solid is collected by filtration and washed with toluene. The solid is suspended in acetone and stirred for an hour. The remaining solid is isolated by filtration, washed with acetone and dried under vacuum. $^1$H, $^{13}$C and $^{19}$F NMR, and mass spectrometry are consistent with the expected product.

This reaction was remarkable in that the reaction occurred very quickly upon addition of the Hünig's base. The other reported reactions were heated above 100° C. to affect the cyclization.

Maleate (cis double bond) was chosen over fumarate (trans double bond) because the maleate functionality should result in a d,l backfunctionalization. The reasoning behind this is due to an assumption on how the formamidine cyclization proceeds. Firstly, the bromination of the maleate is thought to proceed through the standard bromination mechanism where bromine attacks the double bond and forms cyclic bromonium cation. The resulting bromide anion attacks one of the carbons from the back resulting in the d,l dibromide. This is confirmed by NMR spectroscopy where only one isomer is present. Upon addition of the mesityl formamidine and Hünig's base, the reaction did not occur spontaneously like the acrylate based system and some heating was required. After a few hours at 60° C., a white solid was isolated by filtration, suspended in acetone, filtered once again and dried.

$^1$H, $^{13}$C NMR and mass spectrometry suggest that the expected product was formed although the data indicate a mixture of d,l and meso isomers was formed. These results suggest that soluble bromide anion displaced one of the bromides of the d,l dibromo maleate to give the meso dibromo maleate. Confirmation of this displacement includes an experiment wherein d,l dibromide and tetrabutylammonium bromide were heated at 60° C. for several hours (see FIG. 10). The starting d,l dibromo succinate and meso dibromo succinate were both observed.

Example B—Cyclization Specificity

Generally, a scintillation vial was charged with a stir bar, the target formamidine (1.5 g, 1 equivalent), toluene (11 g to 16 g) and Hünig's base (1.2 equivalents). The mixture is set stirring and methyl 2,3-dibromopropionate (1.2 equivalents) was added. The reaction is stirred at 40° C. for four hours. The solid was filtered and washed with toluene. A sample of the solid was taken and analyzed by NMR spectroscopy. Successful reactions showed Hünig's base present and the resonance of the product with a distinct 2-H peak at about δ 11.4 and the three 4,5-H peaks at about δ 6.21, 5.13, and 4.37 (4-CF$_3$-phenyl entry). The exception was the formation of the 2-ethylhexyl imidazolinium salt that is soluble in toluene. Unsuccessful reactions showed only Hünig's base as the solid.

Solids from the successful reactions were washed with acetone, suspended in acetone/water and stirred for an hour. Remaining solid was isolated by filtration, washed with acetone, and dried under vacuum.

$^1$H NMR spectroscopy in CDCl$_3$ exhibited characteristic resonances on a monobackfunctional imidazolinium salt (the distinct 2-H peak at about δ 11.4 and the three 4,5-H peaks at about δ 6.21, 5.13, and 4.37).

Results for the survey are summarized in Table 1, below.

TABLE 1

| ALIPHATIC PRECURSOR | PRODUCT | ADDITIONAL NOTE |
| --- | --- | --- |
| mesityl | imidazolinium product | |
| o-tolyl- | imidazolinium product | |
| p-tolyl- | imidazolinium product | |
| 2,6-diisopropylphenyl- | imidazolinium product | contained starting formamidine |
| 4-CF$_3$-phenyl- | imidazolinium product | |
| 3-CF$_3$-phenyl- | | |
| 2-CF$_3$-phenyl- | | |
| 3,5-(CF$_3$)$_2$-phenyl- | | |
| 2,4,6-trifluorophenyl | | |
| pentafluorophenyl | | |
| adamantyl- | imidazolinium product | contained starting formamidine |
| cyclohexyl- | imidazolinium product | |
| 2-ethyl-1-hexyl-formamidine | imidazolinium product | contained starting Hünig's base, HBr; see Example D - Ionic Liquids |

As shown, cyclization according to embodiments of the present invention may be used for both aromatic formamidines (conventionally common) and aliphatic formamidines.

Example C—Cyclization with Alternative Bases

Because Hünig's base may be economically prohibitive to bulk quantity production, a cyclization of mesityl formamidine with methyl 2,3-dibromopropionate was carried out with triethylamine as the base.

A scintillation vial was charged with a stir bar, the mesityl formamidine (2.00 g, 7.13 mmol), toluene (14 g) and methyl 2,3-dibromopropionate (2.19 g, 8.92 mmol). The mixture was set stirring and triethylamine (0.79 g, 7.85 mmol) was added. The reaction was stirred at 40° C. for four hours. The solid was filtered and washed with toluene and then acetone. The solid was then suspended in water and stirred for an hour. The solid was collected by filtration, washed with acetone, and dried.

The $^1$H NMR spectrum of this product is identical to the product of the Hünig's base reaction in Example B.

Example D—Ionic Liquids

Cyclization of 2-ethyl-1-hexyl formamidine, according to the method described in Example B, resulted in formation of a 2-ethylhexyl imidazolinium salt. This particular product is soluble in toluene and is a viscous oil at room temperature.

A small amount of Hünig's base salt in the mixture that cannot be washed away as the Hünig's base salt is slightly soluble in toluene. The cyclization reaction was rerun using triethylamine as the base (noting that the triethylamine salt is insoluble in toluene).

A round bottom flask was charged with a stir bar, the 2-ethylhexyl formamidine (15.00 g, 55.87 mmol), toluene (75 g) and triethylamine (6.78 g, 67.04 mmol). The mixture was set stirring and methyl 2,3-dibromopropionate (16.49 g, 67.04 mmol) was added. The reaction was stirred at 40° C. for four hours. The mixture was cooled to room temperature and the solid was filtered and washed with toluene and set aside. The filtrate was evaporated at room temperature under vacuum and then heated under vacuum for an hour at 60° C. to drive off any unreacted materials. The liquid was cooled to yield a yellow, viscous oil at room temperature.

$^1$H NNMR exhibits the distinctive peaks of four different imidazolinium 2-H protons centered at δ 10.05 and the three 4,5 protons at δ 4.02, 4.34, and 4.90.

A NEt$_3$.HBr free product was obtained. The base-free product is also an ionic liquid.

The $^1$H NMR spectrum of this product was quite complicated with four different 2-protons present. This phenomenon is due to the fact that there are three diastereotopic centers in the 2-ethylhexyl imidazolinium salt which should result in eight possible diastereomeric combinations, of which four are observable by $^1$H NMR and the other four are NMR equivalent to the observed four. While the imidazolinium ring structure is present for all four observed diastereomers, the presence of these eight molecules reduces the possibility of the order required for crystallization. Addition of another stereocenter (planned) will result in 16 different diastereomers.

Example E—Transesterification by Tetrafluoropropanol

A round bottomed flask was charged with a stir bar, toluene (8 g), methyl ester mesityl imidazolinium bromide (2.00 g, 4.49 mmol), tetrafluoropropanol (2.96 g, 22.45 mmol) and a catalytic amount of p-toluenesulfonic acid. A distillation head was attached and suspension was heated at 60° C. under nitrogen for several hours. The reaction was cooled and the colorless solid filtered, washed with toluene, and dried under vacuum. $^1$H NMR shows starting material as well as the tetrafluoropropyl ester. The resonances are identical to the previously prepared tetrafluoropropyl ester mesityl imidazolinium bromide salt (Example A).

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. An ionic liquid having comprising the formula:

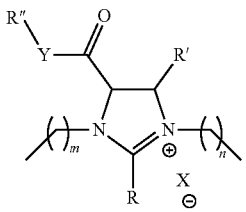

R being a hydrogen or a methyl group;
R' being selected from the group consisting of hydrogen, an ester group, an amide group, and an aromatic group;
R" being selected from the group consisting of an alkyl group and an aromatic group;
the subscript m ranging from 0 to 10;
the subscript n ranging from 0 to 10;
X being a halide or an anion; and
Y being oxygen, sulfur, or NR".

2. The ionic liquid of claim 1, wherein the ionic liquid has a chemical name of 2-ethylhexyl imidazolinium salt.

3. A plasticizer for a propellant formulation, the plasticizer comprising the ionic liquid of claim 1.

4. The plasticizer of claim 3, wherein the propellant formulation further comprises:
ammonium perchorate-based propellants.

5. The plasticizer of claim 3, wherein the propellant formulation further comprises:
ammonium dinitramide-based propellants.

6. The plasticizer of claim 3, wherein the propellant formulation further comprises:
furazan-based propellants.

* * * * *